(12) United States Patent  (10) Patent No.: US 7,888,134 B2
Zeng et al.  (45) Date of Patent: Feb. 15, 2011

(54) IMMUNOSENSORS: SCFV-LINKER DESIGN FOR SURFACE IMMOBILIZATION

(75) Inventors: Xiangqun Zeng, Rochester, MI (US); Raymond L. Mernaugh, Franklin, TN (US)

(73) Assignees: Oakland University, Rochester, MI (US); Vanderbilt University, Nashville, TN (US)

( * ) Notice: Subject to any disclaimer, the term of this patent is extended or adjusted under 35 U.S.C. 154(b) by 551 days.

(21) Appl. No.: 11/890,403

(22) Filed: Aug. 6, 2007

(65) Prior Publication Data
US 2008/0171346 A1   Jul. 17, 2008

Related U.S. Application Data

(63) Continuation-in-part of application No. 10/861,617, filed on Jun. 4, 2004, now Pat. No. 7,329,536.

(60) Provisional application No. 60/476,123, filed on Jun. 5, 2003.

(51) Int. Cl.
*G01N 33/563* (2006.01)
*G01N 33/543* (2006.01)
(52) U.S. Cl. .................... 436/512; 435/7.92; 436/518; 436/524; 436/525; 436/805; 436/809
(58) Field of Classification Search ............... None
See application file for complete search history.

(56) References Cited

U.S. PATENT DOCUMENTS

| 4,242,096 A | 12/1980 | Oliveira et al. |
| 4,246,344 A | 1/1981 | Silver, III |
| 4,314,821 A | 2/1982 | Rice |
| 4,735,906 A | 4/1988 | Bastiaans |
| 4,788,466 A | 11/1988 | Paul et al. |
| 4,999,284 A | 3/1991 | Ward et al. |
| 5,117,192 A | 5/1992 | Hurd |
| 5,201,215 A | 4/1993 | Granstaff et al. |
| 5,233,261 A | 8/1993 | Wajid |
| 5,282,925 A | 2/1994 | Jeng et al. |
| 5,314,830 A | 5/1994 | Anderson et al. |
| 5,484,626 A | 1/1996 | Storjohann et al. |
| 5,616,827 A | 4/1997 | Simmermon et al. |

(Continued)

OTHER PUBLICATIONS

J. Immun. Methods. 242 (2000) 101-114.

(Continued)

*Primary Examiner*—Christopher L Chin
(74) *Attorney, Agent, or Firm*—Ian C. McLeod; Steven M. Parks

(57) ABSTRACT

An apparatus and methods for binding an analyte of interest in a sample are provided. The apparatus comprises a substrate with an exposed surface with an compound, that is electrostatically charged or capable of forming hydrogen bonds, provided bound to the solid substrate. A recombinant single chain antibody (scFv) molecule specific for the analyte of interest, having one or more amino acids with charged or hydrogen-bond forming sidechains in a linker polypeptide portion, is bound to the layer on the solid substrate. When the analyte of interest is present in the sample the scFv binds the analyte to the solid substrate. The apparatus can be used with an immunoglobulin layer to detect Fc receptors, so as to detect microorganisms such as *Staphylococcus aureus* having protein A or protein G.

31 Claims, 21 Drawing Sheets

U.S. PATENT DOCUMENTS

| | | | |
|---|---|---|---|
| 5,706,840 A | 1/1998 | Schneider | |
| 5,795,993 A | 8/1998 | Pfeifer et al. | |
| 5,877,291 A * | 3/1999 | Mezes et al. | 530/387.3 |
| 5,885,402 A | 3/1999 | Esquibel | |
| 5,932,953 A | 8/1999 | Drees et al. | |
| 6,087,187 A | 7/2000 | Wiegland et al. | |
| 6,106,149 A | 8/2000 | Smith | |
| 6,190,035 B1 | 2/2001 | Smith | |
| 6,439,765 B2 | 8/2002 | Smith | |
| 6,492,601 B1 | 12/2002 | Cain et al. | |
| 6,647,764 B1 | 11/2003 | Paul et al. | |
| 6,706,977 B2 | 3/2004 | Cain et al. | |
| 6,848,299 B2 | 2/2005 | Paul et al. | |
| 6,890,486 B2 | 5/2005 | Penelle | |

OTHER PUBLICATIONS

Zeng, X., Analytical Chemistry vol. 79, No. 4, pp. 1283-1289 (2007).

* cited by examiner

IMMUNOSENSORS: SCFV-LINKER DESIGN FOR SURFACE IMMOBILIZATION

CROSS-REFERENCE TO RELATED APPLICATIONS

This application is a continuation-in-part of U.S. patent application Ser. No. 10/861,617, filed Jun. 4, 2004 now U.S. Pat. No. 7,329,536, which claims priority to U.S. Provisional Application Ser. No. 60/476,123, filed Jun. 5, 2003.

STATEMENT REGARDING FEDERALLY SPONSORED RESEARCH OR DEVELOPMENT

This research was supported by grants from the National Institutes of Health (NIH 1R21EB000672-01, 4R33EB000672-02, 5P30 CA68485-07, 5P30 ES00267-36). The U.S. government has certain rights to this invention

BACKGROUND OF THE INVENTION (1) Field of the Invention

The present invention relates generally to single chain fragment variables (scFv) antibody molecules. Specifically, the present invention relates binding scFv antibody molecules on a substrate that can bind an analyte of interest to the surface.

(2) Description of the Related Art

Antibodies and antibody-based reagents are used in immunotherapy and solid phase based applications including biosensors, affinity chromatography, and immunoassays. In 1988, Phage display technology was developed that allows the presentation of large peptide and protein libraries on the surface of filamentous phage, which leads to the selection of antibodies and antibody fragments, with high affinity and specificity to almost any target. The smallest such antibody fragment is the Fv, which is obtained by association of the variable domains of the heavy chain (VH) and the light chain (VL) of the antibody. Without the accompanying Fc region, Fvs can dissociate rapidly into their single domains, VH and VL and results in a complete loss of the function of the Fv. Protein engineering, recombinant DNA cloning and expression techniques allow the production of small Fvs, which have the domains of the heterodimers stabilized in various ways. For example, recombinant Fvs may contain flexible inter- or intra-chain linkers, connector's peptides, or extra disulfide bonds, and they often fully retain the binding specificity and affinity of the corresponding antibody. Many scFvs retain the specificity and have similar affinity with the original antibody or the monovalent Fab fragment. The advantages of the phage-displayed recombinant antibodies over the conventional polycolonal or monoclonal antibodies are quick generation time, cheap production cost, and importantly, accessibility to the antibody DNA for further genetic manipulations. However, their long circulating half-life is a disadvantage for tumor imaging and therapy. Furthermore, without Fc portion, it cannot initiate immunoresponse. Typically, the scFvs were conjugated with a drug to target tumor cells. However, combining scFv with drugs may increase the chance of toxicity.

While the related art antibodies bound to solid substrates, there still exists a need for an improved system that can immobilize scFv to the sensor substrate (such as Au) so that it can bind analytes of interest to a substrate.

SUMMARY OF THE INVENTION

The present invention provides an apparatus comprising: a substrate with an exposed surface; a compound provided as a layer, bound to the solid substrate; and a plurality of recombinant single chain antibodies (scFv's) specific for the target molecule and bound to the compound on the solid substrate, each scFv comprising an antibody variable light chain ($V_L$) polypeptide specific for the target molecule, an antibody variable heavy chain ($V_H$) polypeptide specific for the target molecule, and a linker polypeptide covalently linking the antibody variable light chain ($V_L$) polypeptide to the antibody variable heavy chain ($V_H$) polypeptide, the linker polypeptide having an amino acid sequence comprising one or more amino acids with side chains that bind to the compound, wherein the scFv immobilized on the solid substrate is capable of binding the target molecule, when provided to the apparatus.

In further embodiments of the apparatus, the recombinant single chain antibodies (scFv's) are specific for immunoglobulins as the target molecules, the apparatus further comprising a plurality of the immunoglobulins bound to the scFv molecules so that Fc regions of the immunoglobulins are exposed as a binding layer for Fc receptors. In some embodiments, the target molecules are analytes of interest in a sample and the apparatus detects whether the analyte of interest is present in the sample. In some embodiments of the apparatus, the compound and the amino acid sidechains form electrostatic interactions. In some embodiments, the compound and the amino acid sidechains form hydrogen bonds. In some of the embodiments, the amino acids with sidechains are arginine or tyrosine. In further embodiments, the compound is electrostatically charged. In some embodiments, the compound is an anionic polyelectrolyte or 2-mercaptoethanol. In some of these embodiments, the anionic polyelectrolyte is poly(sodium 4-styrenesulfonate) (PSS) or 11-mercaptoundecanoic acid (MUA). In further embodiments, the substrate is gold. In some preferred embodiments, the apparatus is provided as a binding component of an immunosensor. In some of these embodiments, the immunosensor is a quartz crystal microbalance (QCM) device or a surface plasmon resonance (SPR) device. In still further embodiments, the apparatus is provided as a microtiter plate for an ELISA assay or as an affinity matrix for immunopurification. In still further embodiments, the amino acids with sidechains are separated by one or more spacer amino acids. In further embodiments, the spacer amino acids are selected from the group consisting of glycine and serine. In some embodiments, the amino acid sequence of the linker polypeptide comprises a series of two or more arginine-glycine (RG) repeats. In still further embodiments, the amino acid sequence of the linker polypeptide comprises a sequence selected from the group consisting of SEQ ID NO:1, SEQ ID NO:2, SEQ ID NO:3, SEQ ID NO:4, SEQ ID NO:5, SEQ ID NO:11, and SEQ ID NO:12.

The present invention provides a method of detecting an analyte of interest in a sample comprising: providing the sample; providing an immunosensor device having a component apparatus for binding the analyte of interest in a sample comprising: a substrate with an exposed surface; a compound provided as a layer bound on the solid substrate; and a plurality of recombinant single chain antibodies (scFv's) specific for the analyte of interest bound to the compound on the solid substrate each scFv comprising an antibody variable light chain ($V_L$) polypeptide specific for an analyte, an antibody variable heavy chain ($V_H$) polypeptide specific for the analyte, and a linker polypeptide covalently linking the antibody variable light chain (VL) polypeptide to the antibody variable heavy chain (VH) polypeptide, the linker polypeptide having an amino acid sequence comprising one or more amino acids with sidechains that bind to the compound, wherein when the analyte of interest is present in the sample the scFv binds the analyte to the solid substrate; applying the sample to the apparatus for a time sufficient for the scFv on the substrate to bind to the analyte if present in the sample; and detecting the analyte bound to the scFv on the solid substrate with the immunosensor device. In further embodiments, the immunosensor device is a quartz crystal microbalance (QCM) device or a surface plasmon resonance (SPR) device.

The present invention provides a method of binding an analyte of interest in a sample comprising: providing the sample; providing an apparatus for binding an analyte of interest in a sample comprising: a substrate with an exposed surface; a compound provided as a layer bound on the solid substrate; and a plurality of recombinant single chain antibodies (scFv's) specific for the analyte of interest bound to the compound on the solid substrate each scFv comprising an antibody variable light chain ($V_L$) polypeptide specific for an analyte, an antibody variable heavy chain ($V_H$) polypeptide specific for the analyte, and a linker polypeptide covalently linking the antibody variable light chain (VL) polypeptide to the antibody variable heavy chain (VH) polypeptide, the linker polypeptide having an amino acid sequence comprising one or more amino acids with sidechains that bind to the compound, wherein when the analyte of interest is present in the sample the scFv binds the analyte to the solid substrate; and incubating the sample to the apparatus for a time sufficient for the scFv on the solid substrate to bind to the analyte if present in the sample. In further embodiments, the apparatus is a microtiter plate for an ELISA assay or a microarray. In still further embodiments, the apparatus is an affinity column.

The present invention provides a method of determining whether an analyte with an Fc receptor is present in a sample comprising: providing the sample; providing an immunosensor device having a component an apparatus comprising: a substrate with an exposed surface; a compound provided as a layer, bound to the solid substrate; a plurality of recombinant single chain antibodies (scFv's) specific for an immunoglobulin and bound to the compound on the solid substrate, each scFv comprising an antibody variable light chain ($V_L$) polypeptide specific for the immunoglobulin, an antibody variable heavy chain ($V_H$) polypeptide specific for the immunoglobulin, and a linker polypeptide covalently linking the antibody variable light chain (VL) polypeptide to the antibody variable heavy chain (VH) polypeptide, the linker polypeptide having an amino acid sequence comprising one or more amino acids with sidechains that bind to the compound, wherein the scFv is capable of binding the immunoglobulin to the solid substrate; and a plurality of the immunoglobulins bound to the scFv molecules so that Fc regions of the immunoglobulins are exposed as a binding layer for the Fc receptor; applying the sample to the apparatus for a time sufficient for the scFv on the substrate to bind to the Fc receptor if present in the sample; detecting the Fc receptors in the sample bound to the scFv on the solid substrate with the immunosensor device; and determining whether the analyte is present in the sample by the result in step (d).

In further embodiments of the method, the immunosensor device is a quartz crystal microbalance (QCM) device or a surface plasmon resonance (SPR) device. In further embodiments, the Fc receptor is Protein A or Protein G. In still further embodiments, the analyte with the Fc receptor is *Staphylococcus aureus*. In still further embodiments, the immunoglobulin is IgG.

BRIEF DESCRIPTION OF THE DRAWINGS

FIG. 2A shows the protein A on the surface of the *S. aureus*, which is bound to the Fc portion of IgG.

FIG. 4A depicts ELISA results for A10B scFv-RG3, A10B-RS, scFv-Cys and scFv-His and negative control (scFv I-20 specific for CYP1B1 P450, scFv D 11-Cys specific for isoketal protein adduct, A10B-D2 monoclonal antibody) antibodies on (from left to right in each set) rabbit IgG, human IgG, goat IgG, rat IgG, bovine IgG and bovine serum albumin (BSA).

DETAILED DESCRIPTION OF THE INVENTION

Figure 1:
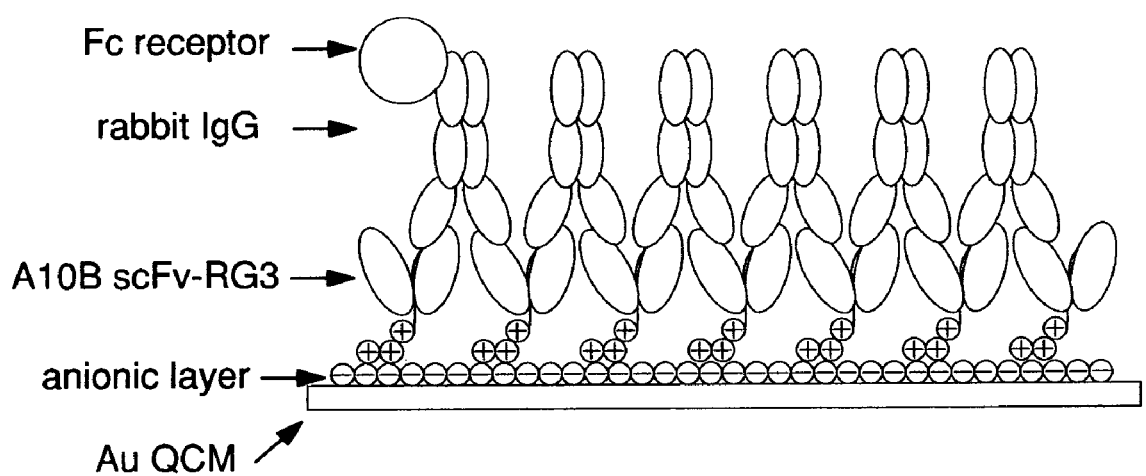
FIG. 1 is a scheme of an idealized representation of the different self-assembled surfaces: MUA/scFv-RG3 Au surface or PSS/scFv-RG3 on a gold (Au) QCM surface.

All patents, patent applications, government publications, government regulations, and literature references cited in this specification are hereby incorporated herein by reference in their entirety. In case of conflict, the present description, including definitions, will control.

The term "bacteria" as used herein refers to include both gram-positive and gram-negative bacteria.

The term "immunosensor" as used herein refers to any immunosensing apparatus such as, but not limited to, quartz crystal microbalance (QCM) devices, surface plasmon resonance (SPR) devices, protein microarrays (ie. antibody microarrays), microbeads, and protein sensor chips.

The term "microorganism" as used herein refers to any microorganism, including but not limited to, bacteria and fungi.

The term "QCM" as used herein refers to a quartz crystal microbalance. Any quartz crystal microbalance devices can be used in the present invention including, but not limited to, QCM devices available from Maxtek Inc. of Santa Fe Springs, Calif. Other QCM devices which can be used in the present invention are described in U.S. Pat. No. 4,236,893 to Rice, U.S. Pat. No. 4,242,096 to Oliveira et al., U.S. Pat. No. 4,246,344 to Silver III, U.S. Pat. No. 4,314,821 to Rice, U.S. Pat. No. 4,735,906 to Bastiaans, U.S. Pat. No. 5,314,830 to Anderson et al., U.S. Pat. No. 5,932,953 to Drees et al., and U.S. Pat. No. 6,087,187 to Wiegland et al., U.S. Pat. No. 6,890,486 to Penelle, U.S. Pat. No. 6,848,299 to Paul et al., U.S. Pat. No. 6,706,977 to Cain et al., U.S. Pat. No. 6,647,764 to Paul et al., U.S. Pat. No. 6,492,601 to Cain et al., U.S. Pat. No. 6,439,765 to Smith, U.S. Pat. No. 6,190,035 to Smith, U.S. Pat. No. 6,106,149 to Smith, U.S. Pat. No. 5,885,402 to Esquibel, U.S. Pat. No. 5,795,993 to Pfeifer et al., U.S. Pat. No. 5,706,840 to Schneider, U.S. Pat. No. 5,616,827 to Simmermon et al., U.S. Pat. No. 5,484,626 to Storjohann et al., U.S. Pat. No. 5,282,925 to Jeng et al., U.S. Pat. No. 5,233,261 to Wajid, U.S. Pat. No. 5,201,215 to Granstaff et al., U.S. Pat. No. 4,999,284 to Ward et al., and U.S. Pat. No. 4,788,466 to Paul et al. Examples of control circuitry for quartz crystal microbalances and methods for detecting materials using piezoelectric resonators are described in U.S. Pat. No. 5,117, 192 to Hurd and U.S. Pat. No. 5,932,953 to Drees et al. Each of the above references are hereby incorporated herein by reference in their entirety.

The term "surface" as used herein refers to any solid surface. In some embodiments, the solid surfaces are QCM electrode surfaces.

The term "SPR" as used herein refers to a surface plasmon resonance. Any SPR device can be used in the present invention including, but not limited to, a Biocore system (GE Healthcare) or the SPR biosensor device as described in U.S. patent application Ser. No. 11/581,260 to Xiao and Zeng.

U.S. patent application Ser. No. 10/861,617 to Zeng et al., hereby incorporated herein by reference in its entirety, discloses an improved piezoimmunosensor. Zeng et al. teach of the single chain fragment variable (scFv)'s capability and potential as a superior new type of immuno-recognition element by protein engineering the metal binding amino acids (i.e. cysteine, histidine and biotin) into the peptide linker which links the heavy ($V_H$) and the light ($V_L$) chain variable domains. This allows the direct immobilization of scFv in their native state on the gold surface and the antigen-binding site is oriented toward the solution phase. Three papers have been published in year 2005, 2006 and 2007 on this topic. Twelve A10B scFv constructs were made as shown in Table 1. Six scFv that is biotinylated were also made for binding with CYp1b1 enzyme. In these embodiments, the recombinant single chain antibody (scFv) molecule utilized in the present invention can comprise a first variable chain polypeptide having a first amino acid sequence with an scFv amino terminus and a carboxy terminus, which is an antibody variable light chain ($V_L$) or an antibody variable heavy chain ($V_H$) polypeptide specific for an analyte of interest; a second variable chain polypeptide having a second amino acid sequence with an amino terminus and an scFv carboxy terminus, which is an antibody variable light chain ($V_L$) or an antibody variable heavy chain ($V_H$) polypeptide specific for the analyte of interest; and a linker polypeptide having a third amino acid sequence comprising one or more amino acids having charged sidechains covalently linking the carboxy terminus of the first variable chain polypeptide to the amino terminus of the second variable chain polypeptide. In some embodiments of the present invention, the recombinant single chain antibody (scFv) molecule further comprises a tagged amino acid sequence at the scFv carboxy terminus. In further embodiments, the recombinant single chain antibody (scFv) molecule further comprises a tagged amino acid sequence at the scFv amino terminus. In further embodiments, the scFv comprises a biotin tag.

We have recently realized the scFv's capability and potential as an superior new type of immuno-recognition elements by protein engineering the metal binding amino acids (i.e. cysteine and histidine) into the peptide linker that links the heavy ($V_H$) and the light ($V_L$) chain variable domains. This allows the direct immobilization of scFv in their native state on the gold surface and the antigen-binding site is oriented toward the solution phase. Our studies show that the specific orientation of scFv antibodies consistently increases the analyte-binding capacity of the surfaces, with up to three-fold improvements over surfaces with randomly oriented monoclonal antibody, five-fold improvements over surfaces with randomly oriented antibody $F_{ab}$ fragments. Literature shows that in many scFvs there seems to be little effect of these linker variations on affinity or stability of the Fv. However, the linker sequence can affect the yield of functional Fvs that are obtained from refolding of inclusion antibodies. For example, it was found that when cysteines and histidines are incorporated into some recombinant scFv antibodies or linkers, scFv antigen-binding activity can be disrupted through inter-scFv disulfide bond formation and scFv aggregation; or scFv bacterial protein expression can be substantially reduced (*J. Immun. Methods*, 242 (2000)101-114).

We also demonstrated scFv with biotin tag for detection of P450 CYP1B1 enzyme, an cancer biomarker (shown in inventor Zeng's publication "Recombinant Antibody Pizeoimmunosensors for the detection of Cytochrome P450 1B1", *Analytical Chemistry* Vol. 79, No. 4, pp. 1283-1289 (2007).

We also demonstrated that the scFv biosensor system can be used to provide a platform immobilization strategy to build rigid IgG Fc receptor layers. Just as importantly, the ability of immunoglobulins to react with other molecules at sites located outside the antigen-combining site, related to the effector functions of antibodies, are the most important part of the immune response. These include from such well-known reactions as the activation of the complement cascade and the activation or the inhibition of cells after binding with the Fc receptors to transportation of immunoglobulins through cell membranes. As shown in FIG. 1, monomeric scFv allows uniform 2:1 binding with rabbit IgG CH1 region, that results in a highly oriented IgG Fc portion pointing toward solution phase for the detection of Fc receptors. This arrangement was proven to be feasible by the detection of protein A, a well used Fc receptor in staphylococcal bacteria cell lysate. Detection of protein A in bacteria lysate is challenging due to the presence of excess antibody in the analyte sample that seriously suppresses the response of an assay by competing for the Fc binding sites on protein A, thereby reducing the sensitivity of the assay. We have demonstrated that the specific orientation of Fc capture agents consistently increases the analyte-binding capacity of the surfaces, with up to a seven-fold improvement over surfaces with randomly oriented capture agents. Randomly attached IgG could not be packed at such a high density and had a lower specific activity. These results emphasize the importance of the immobilization of capture reagents to surfaces such that their binding sites are oriented towards the solution phase.

TABLE 1

A10B scFv constructs

| | | |
|---|---|---|
| A10B-RS | GGGGSGGGGSGGGGS | SEQ ID NO: 9 |
| A10B-cys | CGGGSGGGGSGGGGS | SEQ ID NO: 8 |
| A10B C4 | SHGGHGGGGSGGGGS | SEQ ID NO: 13 |
| A10B C-11 | SHGGHGGGGSGGGGS [has His-tagged (HHHHH; H = histidine) sequence on the C-terminus of the scFv)] | linker: SEQ ID NO: 13 His-tag: SEQ ID NO: 14 |
| A10BMG4 | MGGMSGGGGSGGGGS | SEQ ID NO: 15 |
| A10B YG | YGGYSGGGGSGGGGS | SEQ ID NO: 11 |
| A10B WG | WGGYSGGGGSGGGGS | SEQ ID NO: 12 |
| A10B FP1 | SVSVGMKPSPRP | SEQ ID NO: 4 |
| A10B ZnS4 | VISNHAGSSRRL | SEQ ID NO: 2 |
| A10B Cds6 | PWIPTPRPTFTG | SEQ ID NO: 3 |
| A10B RG3 | RGRGRGRGRGR | SEQ ID NO: 1 |
| A10B Biotinylated | Mouse and rat antibodies contain two naturally occurring lysines which are located near the C-terminus of every antibody light chain variable region. The, free amines located on these two lysines, on other lysines that may be present at other locations in an scFv, or at the scFv amino terminus, can be readily biotinylated using commercially available biotinylation reagents, without destroying the scFv antigen-binding activity or specificity. | |

The present invention applies generally to any technique that utilizes rigid films that are built up for non-label detection, such as QCM or SPR of various reagents from proteins to cells or bacteria. The peptide chain length, amino acid composition, specific sequence, net charge at neutral pH and hydrophobicity, are features that can be used to design an scFv which can be directly immobilized on the gold surface or template surface. For example, 15-mer unmodified peptides, there are about 1024 diverse sequences when considering the twenty common amino acids alone. Thus, the linker peptide design provides huge possibilities for surface coupling methodology. This feature, in conjunction with the real-time, non-labeled characters of QCM and/or SPR, presents a widely applicable protein immobilization technology for investigating the protein-protein interactions in general. This illustrates that QCM can be an indispensable technique in mapping the ligand-receptor interactions that is affordable to most investigators in life science research. The scFv of the present invention can be applied to biosensors, immunosensors, ELISA.

Figure 2A:
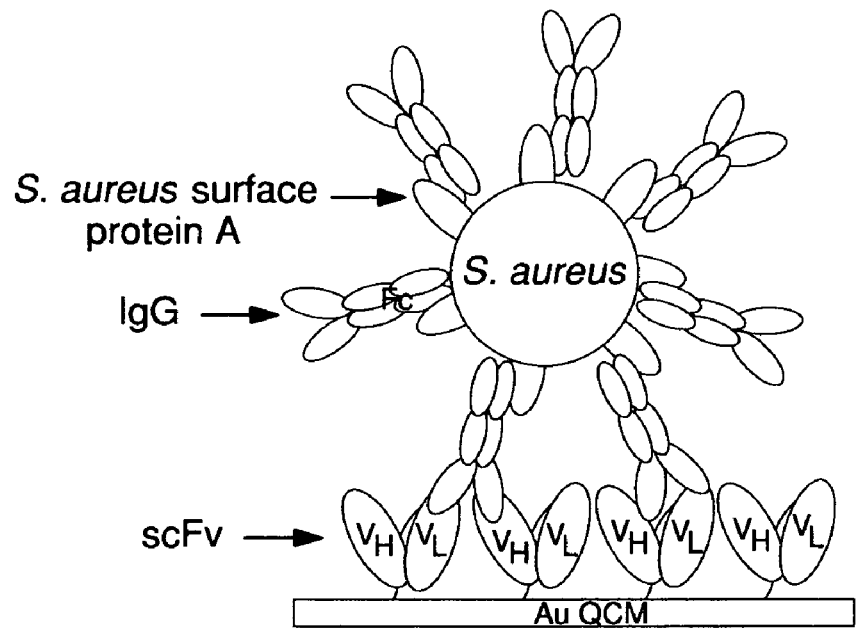
FIGS. 2A and B are schematic representations of the detection of Protein A bacteria, such as *S. aureus* using a sandwich antibody assay for amplification.
Figure 2B:
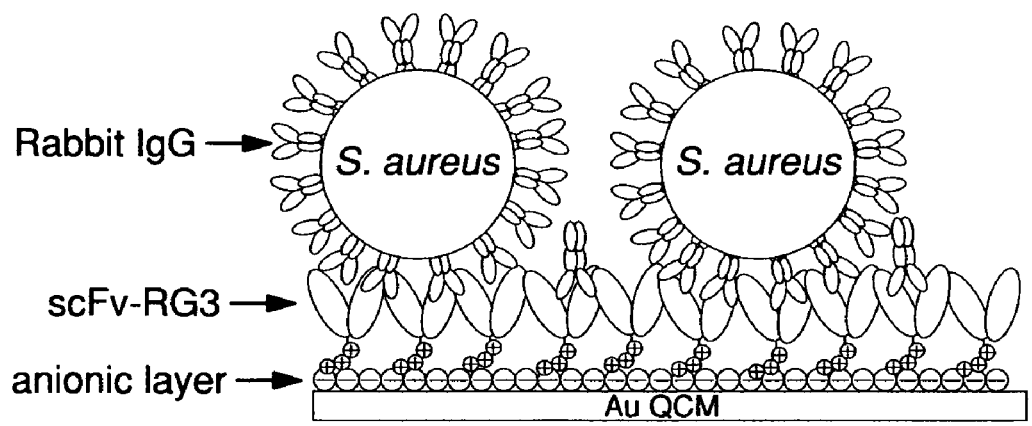
FIG. 2B shows the anionic layer that binds the scFv-RG3 to the gold (Au) surface of the QCM.

In one embodiment, monomeric single chain fragment variable (scFv) molecules allow uniform 2:1 binding with rabbit IgG CH1 region, this results a highly oriented IgG Fc portion pointing toward the solution phase for the detection of Fc receptors. FIGS. 2A and B are schematic representations of the detection of Protein A bacteria, such as *S. aureus* using a sandwich antibody assay for amplification. As illustrated in FIGS. 2A and B, by employing this concept we can detect *Staphylococcus aureus* bacteria with great amplification by binding the rabbit IgG Fc portion to protein A, a membrane protein of *Staphylococcus aureus* bacteria, which is a gram positive bacteria. FIG. 2A shows the protein A on the surface of the *S. aureus*, which is bound to the Fc portion of IgG. FIG. 2B shows the anionic layer that binds the scFv-RG3 to the gold (Au) surface of the QCM.

We have demonstrated that the disadvantages of recombinant antibody observed in immunotherapy work as the benefits for immunosensing i.e. protein microarrays, microbeads, and protein sensor chips. For immunosensing, the intensity of specific signal produced on an immunosensor is related to the amount of analyte that is captured from the biological mixture by the immobilized antibody (ie. the "capture agent"). This in turn is a function of the surface density and fractional activity of the capture agents. The Fc portion is not needed and can detrimentally serve as a non-specific adsorption site. The smaller size of scFvs, as compared to commonly used monoclonal antibodies, increased the surface density and reduces the non-specific adsorption that greatly improved the sensor sensitivity and specificity.

The present invention provides methods for the immobilization of scFvs that does not require the incorporation of cysteine or histidine residues as metal binding amino acids. The immobilization methods take advantage of the limitless flexibility of antibody engineering for the scFvs with the inherent quick, clean, high fidelity characters of surface coupling chemistry (e.g. electrostatic, hydrogen bonding, or covalent attachment) to attach scFvs to pre-formed functionalized self-assembled monolayers. In one embodiment of the present invention, six arginines, which were separated by glycine (G) or serine (S) as spacers, were incorporated in the linker to form a 15-mer peptide linker having the sequence RGRGRGRGRSRGGGS (SEQ ID NO:5). Since arginine contains positive charged side chain at neutral pH and can be immobilized on the surface by electrostatic interaction with the negative charged template. The polycationic peptide was engineered into the A10B scFv model system. In some embodiments of the present invention, two functional template surfaces, poly(sodium 4-sterenesulfonate) (PSS), and 11-mercaptoundecanoic acid (MUA) were used for the specific adsorption of hexa-arginine linked scFv (scFv-RG3). Our results show that the hexa-arginine linked scFv (scFv-RG3) were efficiently adsorbed on the negative charged functional surface via an electrostatic interaction. Different immobilization methods based on the specific peptide linked scFvs were examined, including scFv-GR3/MUA, scFv-RG3/PSS, scFv-RG3/bare-gold, scFv-cys/bare-gold, scFv-His/bare-gold, and scFv-biotin/Avidin methods. The test showed that the scFv-RG3 and MUA coupling method provided the best sensitivity and selectivity.

The location and the generality of above strategies were further studied by engineering addition A10B scFv with positive charged aminoacids into linker peptides. A10B ZnS4 scFv with linker sequence of VISNHAGSSRRL (SEQ ID NO:2), A10B scFv CdS6 with linker sequence of PWIPTPRPTFTG (SEQ ID NO:3), A10B scFv FP1 with linker sequence of SVSVGMKPSPRP (SEQ ID NO:4) were made.

The methods we demonstrated herein can be used for building up rigid films for acoustic detection of various biological antigens from proteins to cell or bacterial. In contrast to SPR technique that has a limit of the thickness of the biofilms, i.e. less than 200 nm, QCM sensor detects only those materials that are acoustically coupled to the sensor surface and theoretically it has no limits regarding the thickness of the film. However, it requires the immobilized biofilms with high rigidity so it can acoustically couple with quartz oscillation. The peptide chain length, amino acid composition, specific sequence, net charge at neutral pH, and hydrophobicity can each be controlled and have dramatic influence on the performance of scFv based QCM sensors. For example, for 15-mer unmodified peptides there are about $10^{24}$ diverse sequences when considering the twenty common amino acids alone. Thus, the linker peptide design provides a huge number of possibilities for a surface coupling methodology. This aspect of the present invention, in conjunction with the real-time, non-labeled character of QCM, presents a widely applicable protein immobilization technology. This can be used for investigating protein-protein interactions in general and promises that QCM will be an indispensable technique in mapping the ligand-receptor interactions, while being affordable to most investigators in life science research.

Example 1

In this example, an A10B scFv RG linker with positively charged RG linkers were successfully used to couple to a negatively charged gold surface. This coupling method has shown the best performance when compared with other linker designs including cysteine and histidine. This approach has broad applicability since a negatively charged linker, such as a linker with arginine amino acid residues, could be coupled to positively charged gold template. The scFv immobilization was based on pre-formed self assemble monolayer (SAM) templates incorporated with various properties. These properties, such as negative charge, positive charge, and hydrogen bonding, can further anchor the scFvs with a linker that is designed to match those interactions on the SAM template to form orientated scFv layers. The immobilized scFvs can be used for protein recognition for clinical and environmental applications, and also can be used to detect bacteria.

Chemicals and materials: Rabbit IgG (cat# 1-5006), bovine serum albumin (BSA, cat# A-4503), goat anti-rabbit IgG (cat# R-2004), and goat anti-human IgG (cat# I-3382) were purchased from Sigma Inc. Goat anti-rabbit IgG Fab fragment (cat# 111-007003) was purchased from Jackson Immunolabs. Peptides RGRGRGRGRSRGGGS (SEQ ID NO:5) and RGRG (SEQ ID NO:6) were purchased from Openbiosystems Inc. The peroxidase conjugated Anti-E tag monoclonal antibody (cat# 27941301) was obtained from Amersham. Poly(sodium 4-sterenesulfonate) (PSS, cat# 527483, MW:70,000), 11-mercaptoundecanoic acid (MUA, cat# 450561), 1-Dodecanethiol, (cat# 471364) were purchased from Sigma-Aldrich. Phosphate buffered saline (PBS), pH 7.2 (Gibco BRL #20012-027), fetal bovine serum (FBS) (Gibco BRL #16000-044). All other chemicals (Aldrich) are reagent grade and used as received.

Preparation and purification of Anti Rabbit IgG ScFv, clone A10B RG3: Modified anti rabbit IgG scFv from clone A10B RG3 with the RGRGRGRGRSRGGGS linker (SEQ ID NO:5) was tested by ELISA. Data confirmed these scFv is highly specific, efficient and effective against rabbit IgG. The bacterial clone producing A10B RG3 scFv reacted with rabbit IgG was inoculated and cultured in 500 ml of 2×YT+AG medium which contains Bacto Tryptone 17 g, Bacto Yeast extract 10 g, sodium chloride 5.0 gm Ampicillin 100 mg and Glucose 20 g per liter. *E. coli* bacteria were incubated at 30° C. overnight with shaking at 125 rpm and then centrifuged down to pellet bacterial cells. The cell pellet was then re-suspended in 500 ml of 2×YT+AI (Ampicillin and IPTG 1 mM) medium and then incubated at 30° C. with shaking at 125 rpm overnight. The periplasmic extract was made by incubating bacterial pellet in 25 ml of 1×TES and 46 ml of ⅕ TES. Well re-suspended suspension was then placed on ice for at least one hour by vigorous shaking. The cell lysate was centrifuged at 5,000 rpm. Anti-E tag affinity columns used for purifying the supernatants containing soluble E-tagged scFv. The concentration of purified scFv was tested by spectrophotometer at $OD_{280}$ nm. The specificity and binding activity of this purified scFv antibody to rabbit IgG was analyzed by Enzyme-Linked Immunosorbent Assay (ELISA).

Recombinant scFv characterization by ELISA: ELISA was used to characterize the soluble recombinant scFv antibody A10B-RG3. Wells of a 384 well microtiter plate (Nunc Cat. # 242757) were coated with serial diluted rabbit IgG. Diluted soluble scFv antibody A10B-RG3 with RGRGRGR-GRSRGGGS (SEQ ID NO:5) linker at the concentration of 2 µg/ml was applied to wells of a microtiter plate that was pre-coated with Rabbit IgG. Since the A10B scFv has an E-tagged stemming from the rodent library, the scFv bound to antigen was detected with the horseradish peroxidase (HRP)-conjugated anti-E tag monoclonal antibody (GE Healthcare), i.e. hydrogen peroxide and ABTS as a color indicator was then finally added to wells. A microtiter plate reader, operating at 405 nm, was used to determine the absorbance readings for each well in an ELISA and the results of the antigen-binding activity was analyzed.

A10B ScFv immobilization: The non-polished gold quartz surface was cleaned sequentially with mixed concentrated acid solution ($H_2SO_4$/$HNO_3$ in 1:1 v/v), biograde water, and ethanol three times. Then, the surface was rinsed with biograde water and dried with nitrogen. The freshly washed gold surface was first immersed either into 4 mM MUA solution overnight or in 2 mg/ml PSS solution for 1-2 hours to form self-assembly anionic charged layer. The anionic charged gold surface was then immersed into A10B scFv-RG3 solution for 8 hours, followed by the treatment of blocking reagent, 0.1% BSA, for 0.5 hour. After the incubation, the excess scFvs on the surface of QCM was washed away with PBS buffer and biograde water. The MUA/scFv-RG3 or PSS/scFv-RG3 modified surface was dried under nitrogen, and used for the detection. A similar procedure was applied to form the PSS/scFv-RG3 modified surface.

QCM measurements: The gold quartz crystal electrode used through out this example was AT cut quartz that coated with 1000 Å gold in an approximate 0.23 $cm^2$ geometric area (International Crystal Company, Oklahoma). It was cleaned as above and modified with scFvs. Then it was mounted in a Kel-F cell sealed by two O-rings and filled with 1 mL PBS buffer. The cell was continuously stirred during the measurement and was placed in a Faraday cage to reduce the potential electromagnetical noise. The frequency change and the damping resistance change caused by the analyte addition were monitored by the Network/Spectrum/Impedance Analyzer (Agilent 4395A).

Electrochemical Characterization: The gold QCM electrode was used as the working electrode. A platinum wire and a saturated calomel electrode (SCE) were used as counter and reference electrodes respectively. Cyclic voltammetry (CV) and electrochemical impedance spectroscopy (EIS) were carried out in a solution of 0.1 M $NaClO_4$ containing 1 mM $K_3Fe(CN)_6$/$K_4Fe(CN)_6$ and performed using a Parstat 2263 advanced electrochemical system (Princeton Applied Research).

Results and Discussion.

HRP ELISA quantification and characterization of A10B scFvs: All A10B-scFv have an E-tag incorporated into the amino terminus of the protein (E-tag: GAPVPYPDPLEPR, SEQ ID NO:7) stemming from the rodent library. An E-tag is a specific linear epitope recognized by commercially available HRP-conjugated anti-E-tag antibody, thus providing a means for a HRP ELISA assay to characterize the affinity and specificity of the binding of A10B-scFvs with rabbit IgG.

Figure 3A:
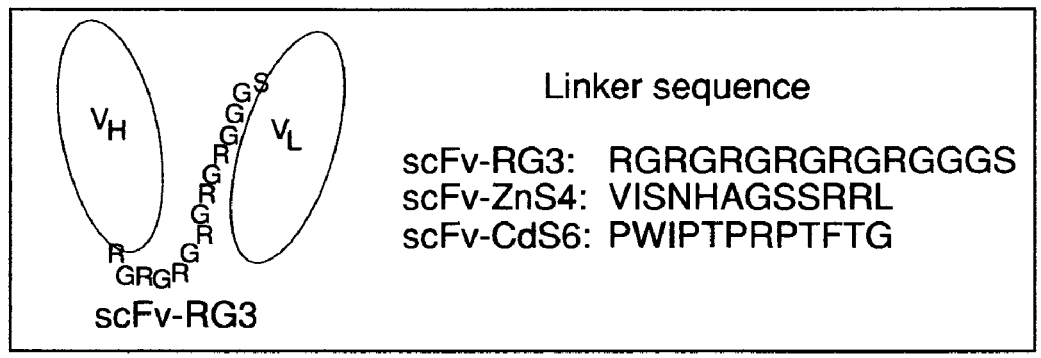
FIG. 3A illustrates an idealized representation of scFv-RG3 with the linker sequence RGRGRGRGRSRGGGS (SEQ ID NO:5). The linker sequences for scFv-RG3, scFv-ZnS4 and scFv-CdS6 are shown on the right.
Figure 3B:
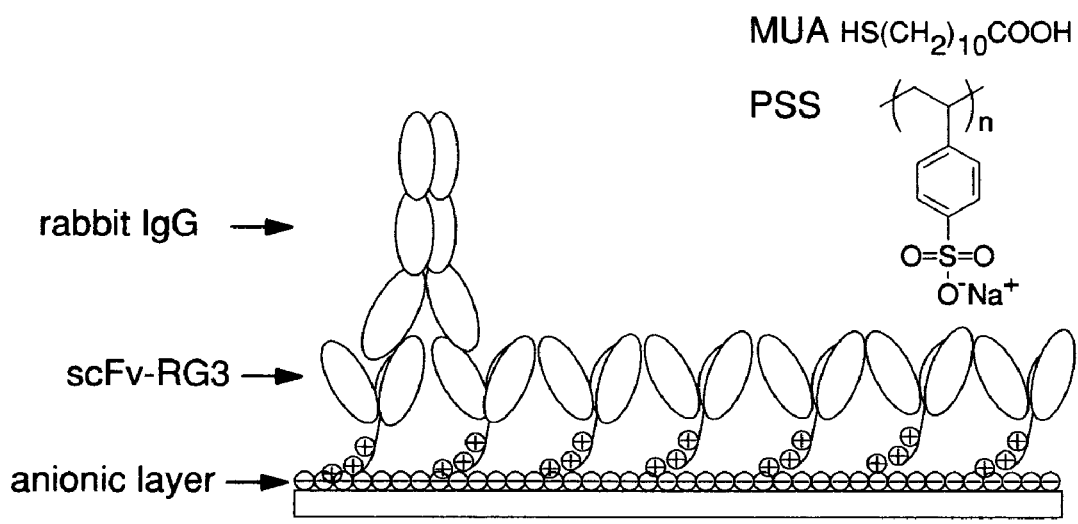
FIG. 3B show idealized representations of the different self-assembled surfaces: MUA/scFv-RG3 Au surface or PSS/scFv-RG3 or Au surface.

FIG. 3A illustrates an idealized representation of scFv-RG3 with the linker sequence RGRGRGRGRSRGGGS (SEQ ID NO:5). The linker sequences for scFv-RG3, scFv-ZnS4 and scFv-CdS6 are shown on the right. FIG. 3B show idealized representations of the different self-assembled surfaces: MUA/scFv-RG3 Au surface or PSS/scFv-RG3 or Au surface. The chemical formulas for MUA and PSS for the anionic layer are shown in the upper right.

Figure 4A:
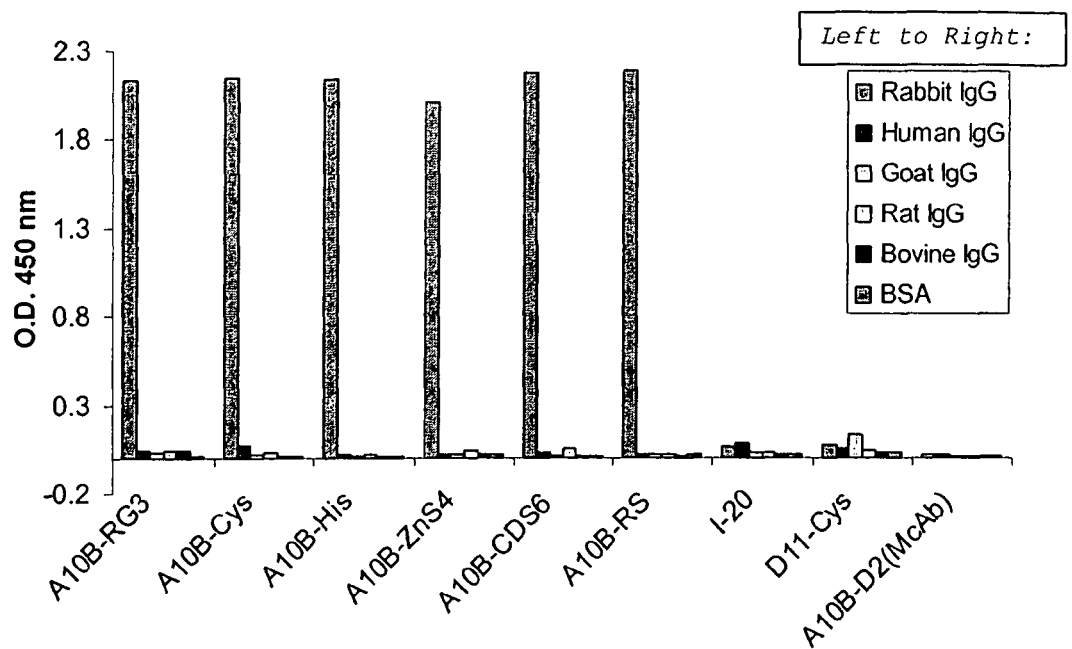
FIGS. 4A and B are graphs that show the characterization of A10B scFv-RG3 (A10B-RG3), scFv-cys (A10B-Cys), scFv-His (A10B-His), scFv-ZnS4 (A10B-ZnS4), scFv-CDS6 (A10B-CDS6), scFv-F11, scFv-RS (A10B-RS) antibodies using HPR ELISA.
Figure 4B:
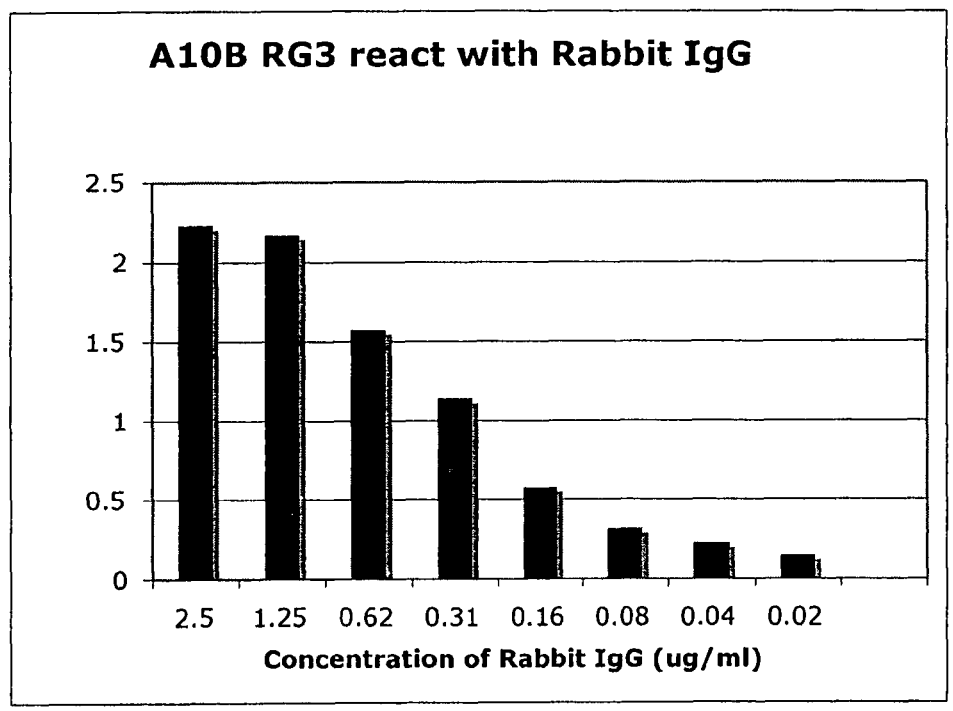
FIG. 4B depicts ELISA results for varying concentrations of rabbit IgG binding with A10B RG3.

FIGS. 4A, and B illustrate the characterization of A10B scFv RG3, scFv-cys, scFv-his, scFv-ZnS4, scFv-CDS6, scFv-F11, scFv-RS antibodies using HPR ELISA. FIG. 4A depicts ELISA results for A10B scFv RG3, A10B RS, scFv-cys and scFv-his and negative control (scFv I-20 specific for CYP1B1 P450, scFv D 11-cys specific for isoketal protein adduct, A10B D2 monoclonal antibody) antibodies on (from left to right) rabbit IgG, human IgG, goat IgG, rat IgG, bovine IgG and bovine serum albumin (BSA). FIG. 4A shows that anti E-tag affinity purified A10B scFv antibodies (i.e. A10B scFv-RG3, scFv-Cys, scFv-His, scFv-ZnS4, scFv-CDS6, scFv-F11, and scFv-RS) specifically bind to antigen rabbit IgG. A10B scFv-RG3, scFv-Cys, scFv-His, scFv-CDS6, and scFv-RS have similar affinity to rabbit IgG. A10B scFv-ZnS4 and A10B scFv-F11 have relative smaller affinity to rabbit IgG. Additionally, little non-specific interaction with other antigens (i.e. IgGs of human, goat, rat and bovine) were observed by all A10B scFvs studied. This ELISA result shows that the modification of A10B scFv linker has little effect on A10B scFv antigen binding affinity and specificity to rabbit IgG antigen. FIG. 4B depicts ELISA results for varying concentrations of rabbit IgG binding with A10B RG3. FIG. 4B shows that the binding activity of A10B scFv-RG3 to rabbit IgG is dose-dependent and as low as 20 ng of rabbit IgG antigen can be detected by A10B scFv-RG3.

Figure 5A:
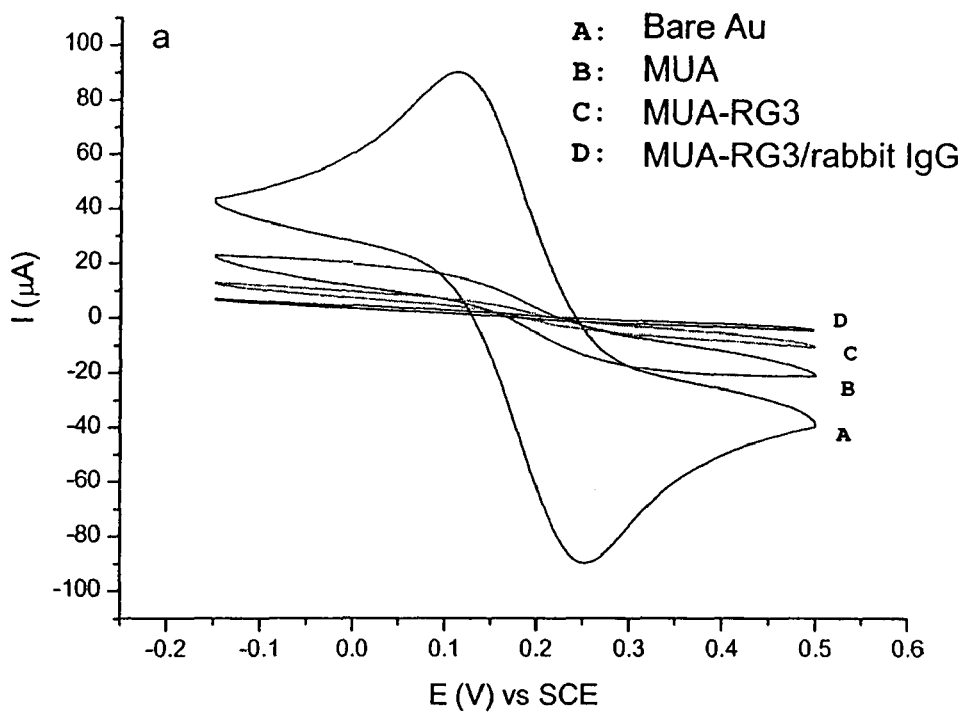
FIG. 5A shows CVs of 1 mM $K_4Fe(CN)_6/K_3Fe(CN)_6$ in 0.1 M $NaClO_4$ on bare gold electrode, MUA, MUA/RG3, and MUA/RG3 binding with rabbit IgG modified electrodes. Scan rate, 50 mV/s.
Figure 5B:
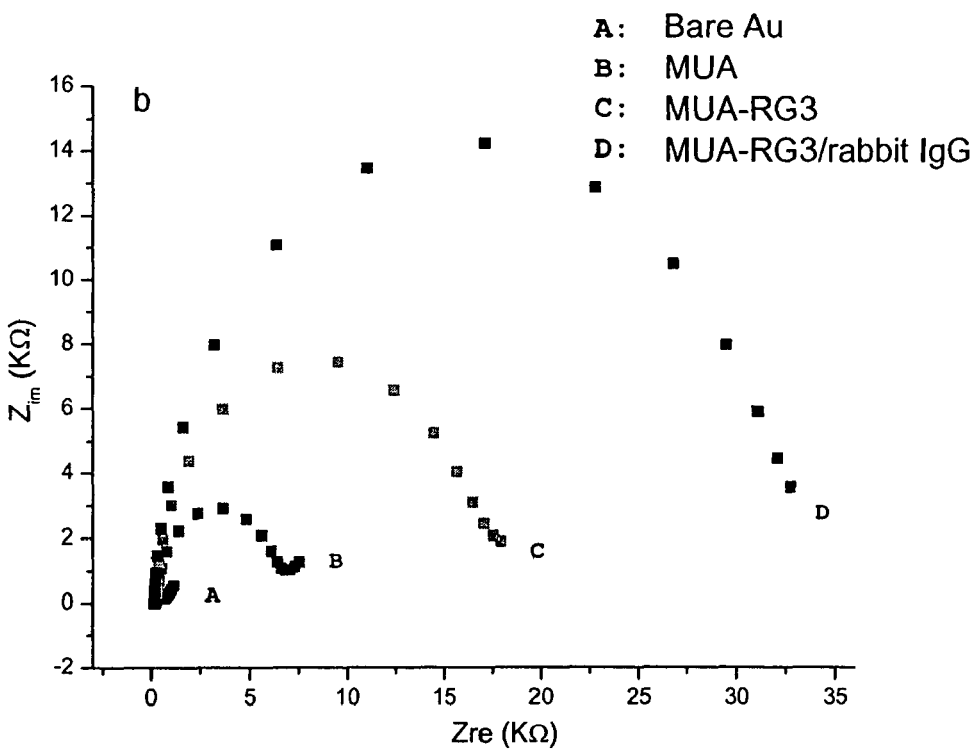
FIG. 5B shows EIS Nyquist plots. Frequency range is 0.1 Hz-100 kHz. Bias potential equals to open circuit potential. AC amplitude is 10 mV.

Electrochemical Characterization of the MUA/scFv-RG3 Biosensor: The integrity of MUA/scFv-RG3 SAM and detection of rabbit IgG was probed by cyclic voltammetry and electrochemical impedance. $K_4Fe(CN)_6$/$K_3Fe(CN)_6$ solution was used as electrochemical probe to test the surface integrity. FIG. 5A shows CVs of 1 mM $K_4Fe(CN)_6$/$K_3Fe(CN)_6$ in 0.1 M $NaClO_4$ on bare gold electrode, MUA, MUA/RG3, and MUA/RG3 binding with rabbit IgG modified electrodes. Scan rate, 50 mV/s. As shown in FIG. 5A, CV on the bare gold surface gave reversible redox peaks. The Faradaic current was dramatically decreased once a SAM of MUA was formed on the gold (Au) surface and further attenuated when scFv-RG3 was coupled onto the MUA SAM and bound with rabbit IgG. The electrochemical impedance spectroscopy was also used to text the surface passivation to electron transfer. FIG. 5B shows EIS Nyquist plots. Frequency range is 0.1 Hz-100 kHz. Bias potential equals to open circuit potential. AC amplitude is 10 mV. As shown in Nyquist plots (FIG. 5B), while the electron-transfer resistance ($R_{et}$) of the $Fe(CN)_6^{IV}$/$Fe(CN)_6^{III}$ redox reactions increased drastically after the formation of the MUA SAM, and further increased when scFv-RG3 was adsorbed onto MUA surface, and bound with rabbit IgG. These experiments supported the existence of highly packed MUA/scFv-RG3 layers and the binding of surface scFv to its corresponding antigen.

Figure 6A:
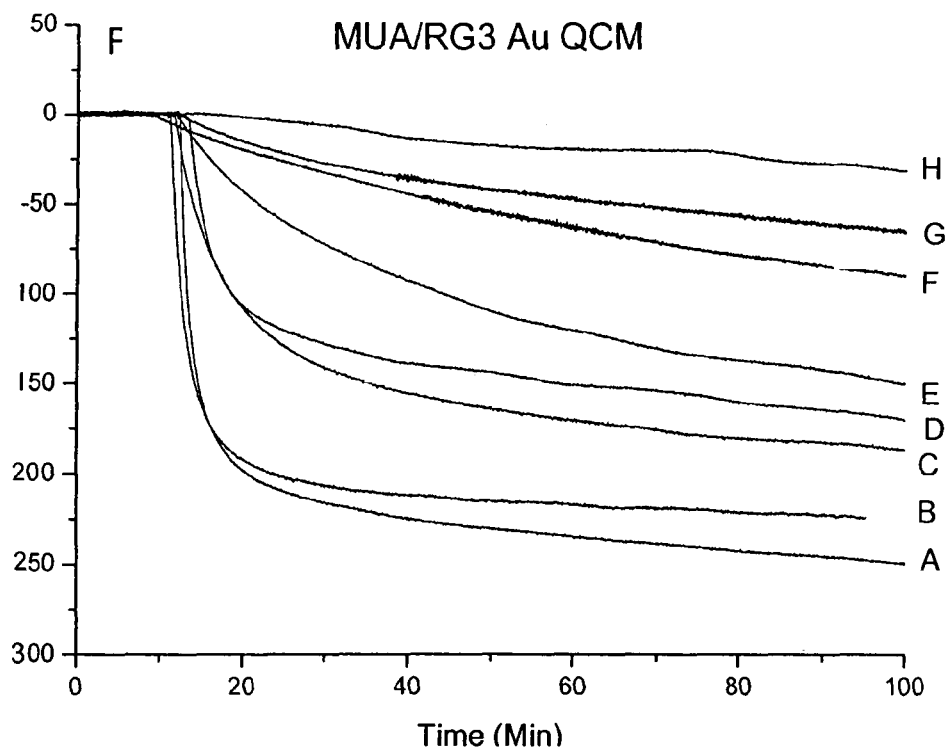
FIG. 6A shows frequency change vs. time
Figure 6B:
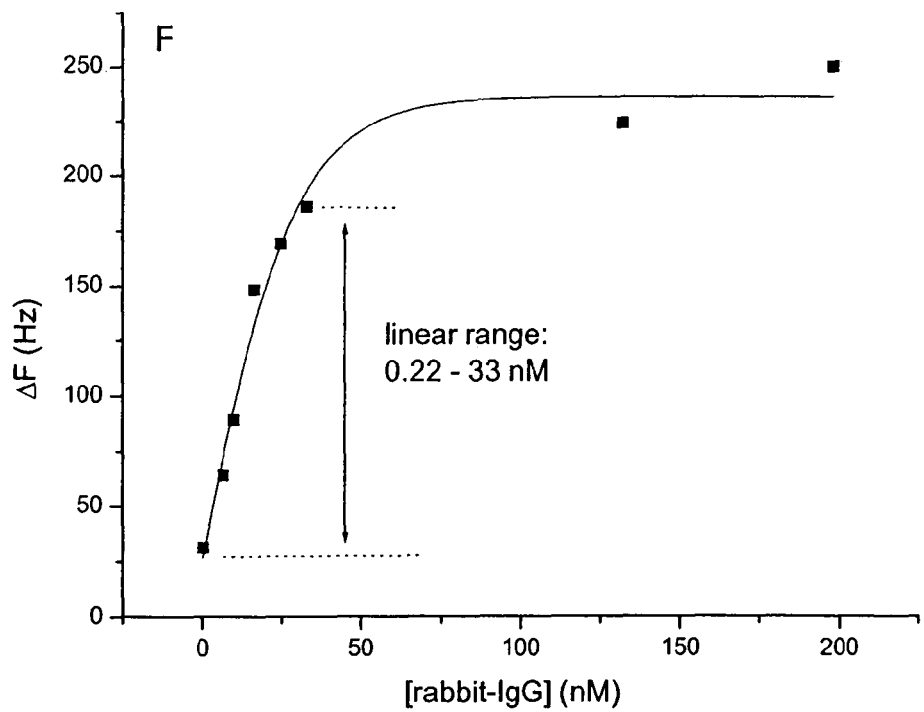
FIG. 6B shows frequency change vs. [rabbit IgG]$_0$ when various concentrations of rabbit IgG were added to the MUA/scFv-RG3 modified Au QCM electrodes. Final concentrations of rabbit IgG were from 0.22 nM to 132 nM (FIG. 6A, B) in 1 ml PBS buffer. The solutions were stirred during all the measurements.

A10B scFv RG3 QCM sensor sensitivity to rabbit IgG: The A10B scFv RG3 specific binds the CH1 region of rabbit IgG. HRP ELISA results above show it has excellent sensitivity and specificity to rabbit IgG. As a result, the A10B scFv RG3 QCM sensors immobilized either through MUA or PSS template was used to detect rabbit IgG with varying concentrations. FIG. 6A shows frequency change vs. time and FIG. 6B shows frequency change vs. [rabbit IgG]$_0$ when various concentrations of rabbit IgG were added to the MUA/scFv-RG3 modified Au QCM electrodes. Final concentrations of rabbit IgG were from 0.22 nM to 132 nM in 1 ml PBS buffer. The solutions were stirred during all the measurements. FIG. 6A show the typical time course of frequency decrease in the presence of various concentrations of rabbit IgG for the MUA/scFv-RG3 sensor. A linear relationship ranging from 0.22 nM to 33 nM was obtained by plotting the frequency changes versus the concentrations of rabbit IgG (FIG. 6B) for MUA/scFv-RG3 sensor, and 0.33 nM to 33 nM for PSS/scFv-RG3 sensors. The frequency change saturated when the concentration of rabbit IgG approached approximately to 132 nM.

Figure 7:
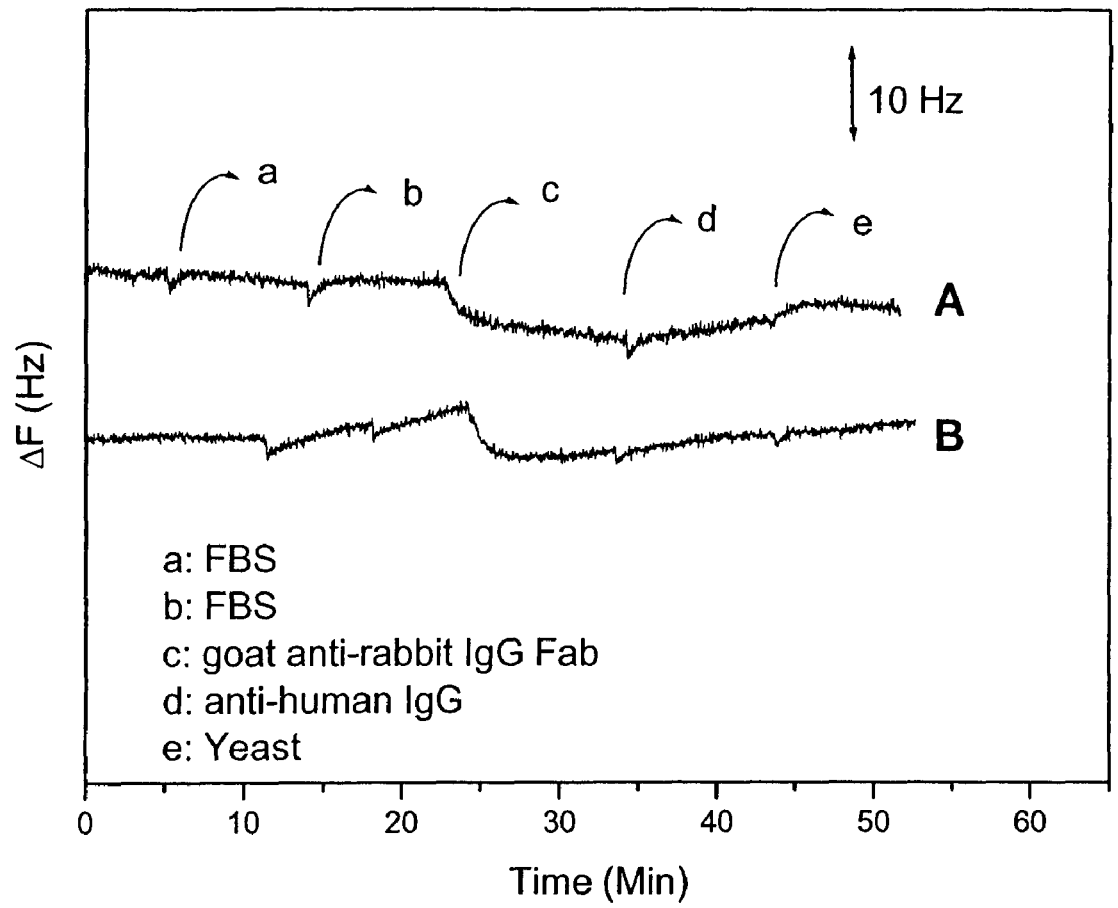
FIG. 7 shows frequency change vs. time curves when (a) FBS, (b) goat anti rabbit IgG Fab, (c) anti human IgG, and (d) yeast; curve B: rabbit IgG were added to PSS/scFv-RG3 (Curve A) and MUA/scFv-RG3 (Curve B) modified Au QCM sensor cells in 1 ml PBS buffer.

A10B scFv-RG3 QCM sensor specificity: The specificity of PSS/scFv-RG3 and MUA/scFv-RG3 QCM sensors were examined by adding the following negative control reagents (i.e. FBS, goat anti rabbit IgG Fab, anti human IgG, and yeast) to the detection cells. FIG. 7 shows frequency change vs. time curves when (a) FBS, (b) goat anti rabbit IgG Fab, (c) anti human IgG, and (d) yeast; curve B: rabbit. IgG were added to PSS/scFv-RG3 (Curve A) and MUA/scFv-RG3 (Curve B) modified Au QCM sensor cells in 1 ml PBS buffer. Shown in FIG. 7, very small nonspecific response signals were observed for all selected control reagents. These results indicate that the MUA/scFv-RG3 and PSS/scRV-RG3 modified QCM sensors exhibit excellent antigen specificity.

Figure 8:
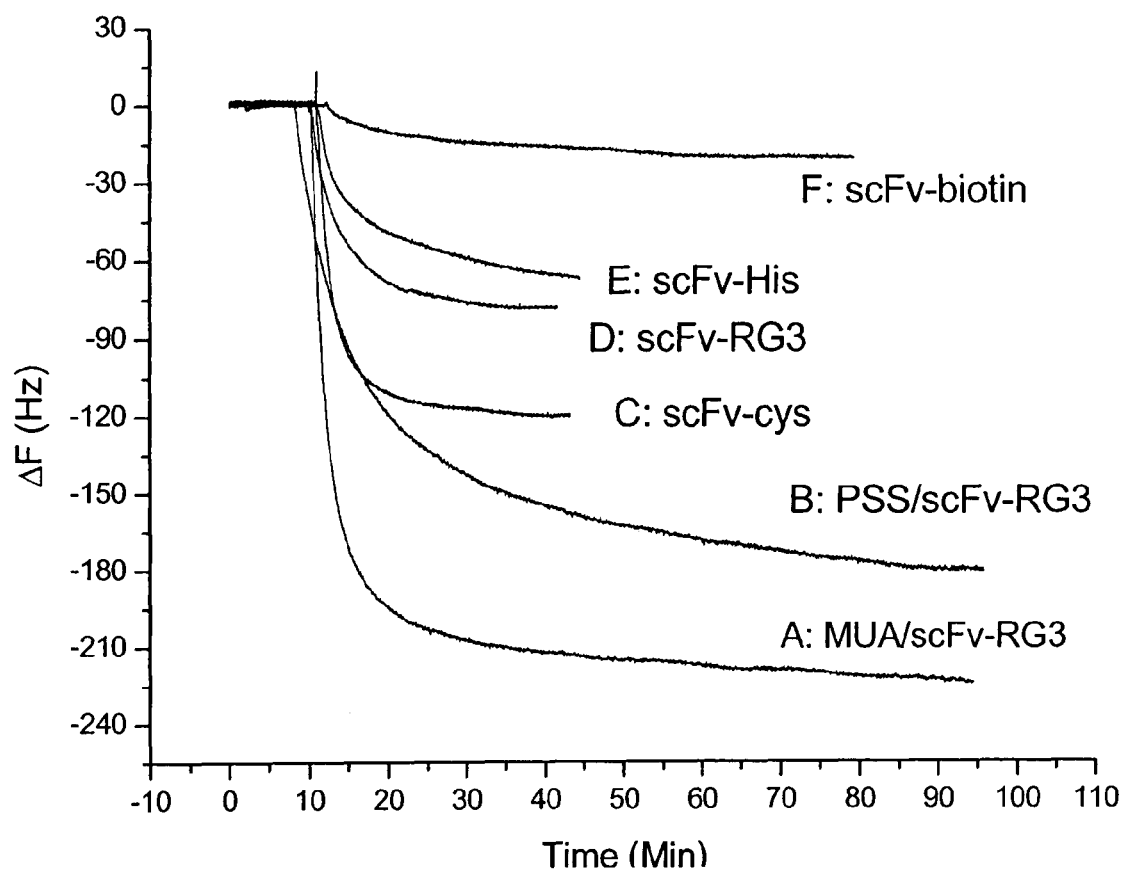
FIG. 8 is a comparison of scFv based QCM sensors' sensitivity. A) MUA/scFv-RG3 B) PSS/scFv-RG3, C) scFv-cys, D) scFv-RG3, E) scFv-His, and F) scFv-biotin pre-coated surfaces. All modified QCM sensors were exposed to 132 nM rabbit IgG.

Comparison of A10B scFv-RG3 sensors to A10B scFv-Cys, scFv-His, and scFv-biotin modified QCM sensors for sensitivity and detection limit: The performances of scFv-RG3 QCM sensors immobilized through electrostatic adsorption on negative charged PSS or MUA template were compared with those early QCM sensors modified by direct adsorption of scFv-Cys, scFv-RG3, scFv-His on gold surface and adsorption of scFv-biotin on the pre-coated avidin gold surface. FIG. 8 is a comparison of scFv based QCM sensors' sensitivity. A) MUA/scFv-RG3 B) PSS/scFv-RG3, C) scFv-cys, D) scFv-RG3, E) scFv-His, and F) scFv-biotin on pre-coated surface. All above modified QCM sensors were exposed to 132 nM rabbit IgG. These six different modified QCM gold electrodes were exposed to the 132 nM rabbit IgG solution (FIG. 8). MUA/scFv-RG3 modified sensors gave the largest frequency decrease and the lowest detection limit (0.22 nM). It is eight to ten fold enhancement compared to scFv-Cys QCM sensor and scFv-His QCM sensor. The PSS/scFv-RG3 gave the second best sensitivity. These results indicated that monolayer negative charged MUA template allows better oriented immobilization of scFv RG3 than the anionic polyelectrolyte template. However, both A10B RG3 surface shows superior sensitivity to the earlier engineered A10B scFv-Cys, A10B scFv-His and A10B scFv-biotin indicating the RG3 linker design is effective to be incorporated into scFv for sensor application.

Figure 9:
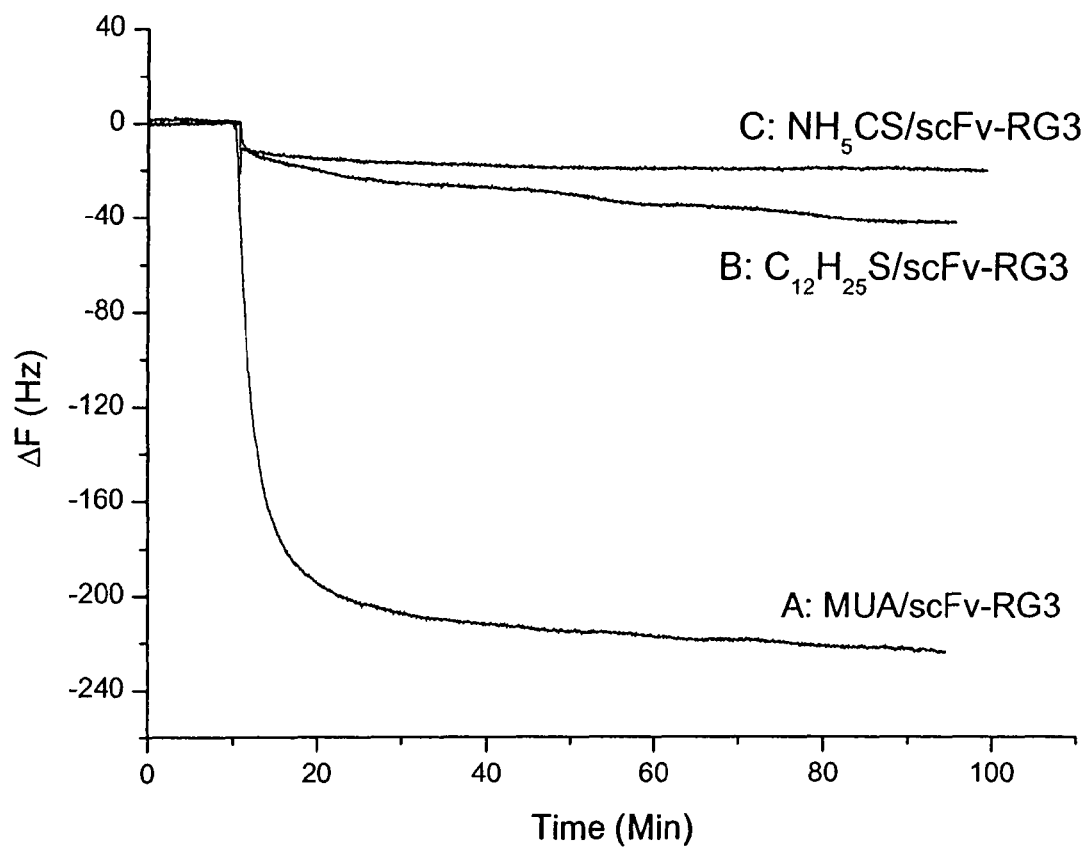
FIG. 9 are frequency change vs. time curves when MUA/scFv-RG3, $C_{12}H_{25}SH$/scFv-RG3, and $NH_5CS$/scFv-RG3 modified QCM sensors were exposed to the 132 nM rabbit IgG.

Template effect and A10B scFv Linker sequence effect: Above studies clearly indicated that scFv-RG3 successfully immobilized onto anionic templates, and the resulting QCM biosensor exhibited excellent sensitivity and selectivity. To further prove that scFv-RG3 was immobilized onto anionic template through electrostatic interaction, two other templates, a neutral template and a cationic template were tested and compared with MUA SAM. For the neutral template, a long chain alkenthiol, 1-dodecanethiol was used to form SAM. For the cationic template, cysteamine, which contained a terminal cationic group, was used. These three sensors ($C_{12}H_{25}SH$/scFv-RG3, $NH_2CH_2SH$/scFv-RG3, and MUA/scFv-RG3) were first treated with scFv-RG3, followed by the addition of the same concentration rabbit IgG. FIG. 9 shows frequency change vs. time curves when MUA/scFv-RG3, $C_{12}H_{25}SH$/scFv-RG3, and $NH_5CS$/scFv-RG3 QCM sensors were exposed to the 132 nM rabbit IgG. As shown in FIG. 9, scFv-RG3 through anionic template (MUA/scFv-RG3) gave the largest signal response (~224 Hz). ScFv-RG3 immobilized through neutral template and cationic template showed much weaker adsorption and bound with rabbit IgG poorly (40 Hz and 20 Hz respectively). These studies demonstrated that the RG3 peptide provides an excellent cationic adsorption sites to be immobilized on cationic template.

Figure 10:
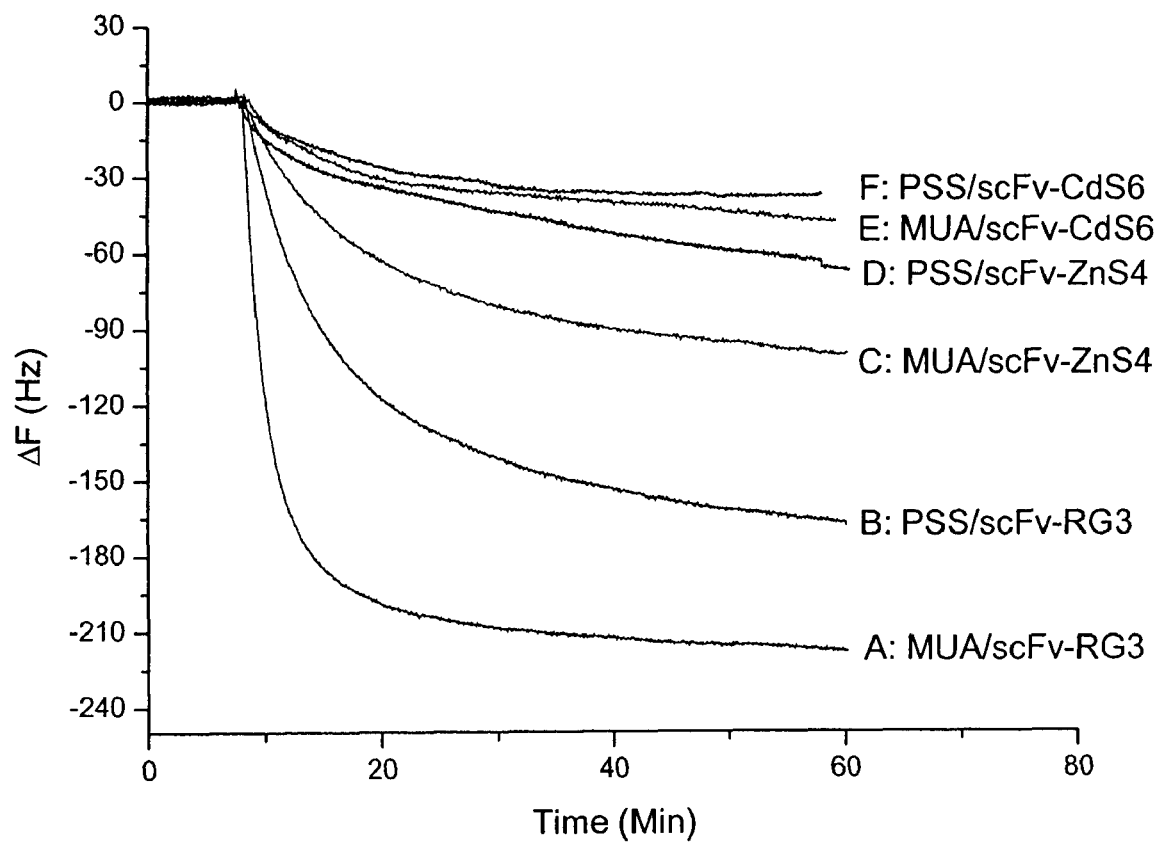
FIG. 10 are frequency change vs. time curves when different modified QCM sensors were exposed to the 132 nM rabbit IgG. A) MUA/scFv-RG3, B) PSS/scFv-RG3, C) MUA/scFv-ZnS4, D) PSS/scFv-ZnS4, E) MUA/scFv-CdS6, and F) PSS/scFv-CdS6 modified QCM sensors.

Encouraged by the good sensitivity and specificity of this anionic template based QCM sensor, more studies were conducted to understand whether the multitude positive charged arginine and their positions as well as the use of spacer glycine are critical for the scFv-RG3 adsorbed on the anionic charged gold surface. Consequently, the scFvs with other linkers contained one or two arginines at different locations, scFv-CdS6 (Linker: PWIPTPRTFTG, SEQ ID. NO:3) and scFv-ZnS4: (Linker: VISNHAGSSRRL, SEQ ID NO:2), were made. Identical procedures were applied to immobilize them on MUA or PSS positive charged surface.—FIG. 10 shows frequency change vs. time curves when different QCM sensors were exposed to the 132 nM rabbit IgG. A) MUA/scFv-RG3, B) PSS/scFv-RG3, C) MUA/scFv-ZnS4, D) PSS/scFv-ZnS4, E) MUA/scFv-CdS6, and F) PSS/scFv-CdS6 modified QCM sensors. FIG. 10 shows that the scFv-RG3 gave the largest response, scFv-CdS6 produced relative smaller response, and scFv-ZnS4 had the smallest response for the addition of 132 nM rabbit IgG. Presumably, the location and the number of arginines played very important roles in the immobilization of the scFvs.

Comparison of different engineered scFvs affinity constant to A10B scFv RG3: The binding between scFv-RG3 and rabbit IgG can be described as Equation 1:

$$[\text{rabbit-IgG}] + [\text{scFv-RG3}] \underset{K_{off}}{\overset{K_{on}}{\rightleftarrows}} [\text{scFv/IgG-complex}] \quad (1)$$

Based on Langmuir adsorption isotherm, association constant ($K_a$) and dissociation constant ($K_d$) for the binding between IgG and scFv-RG3 can be evaluated by Equation 2:

$$\frac{[\text{rabbit-}IgG]_0}{\Delta M} = \frac{[\text{rabbit-}IgG]_0}{\Delta M_{max}} + \frac{1}{\Delta M_{max} K_a} \quad (2)$$

Figure 11:
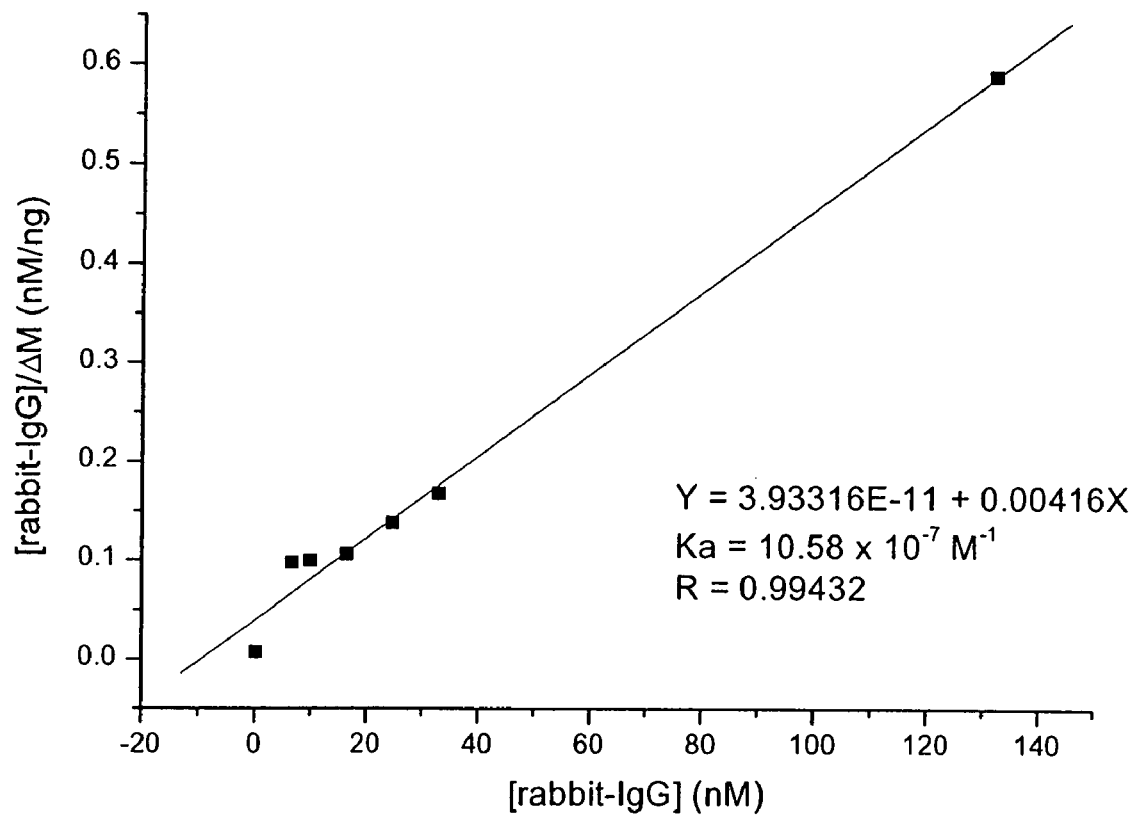
FIG. 11 is a plot of [rabbit-IgG]$_0$/$\Delta$M vs. [rabbit-IgG]$_0$ for MUA/scFv-RG3 modified QCM sensor.

In this equation, $\Delta M_{max}$ is the maximum binding amount, $\Delta M$ is the measured binding amount, and $[\text{rabbit-IgG}]_0$ is the original concentration of rabbit IgG. For these scFv-RG3 based QCM sensors, plotting $[\text{rabbit-IgG}]_0/\Delta M$ vs. $[\text{rabbit-IgG}]_0$ by using the data obtained from FIG. 6A.—FIG. 11 shows the plot of $[\text{rabbit-IgG}]_0/\Delta M$ vs. $[\text{rabbit-IgG}]_0$ for MUA/scFv-RG3 modified QCM sensor. As shown in FIG. 11, a linear relationship was obtained. According to Equation 2, the ratio of the slope to the intercept gave the association constant $K_a$ which were $9.58 \times 10^7$ $M^{-1}$ for PSS modified surface, $10.58 \times 10^7$ $M^{-1}$ for MUA modified surface. $K_d$ was calculated as $1/K_a$. Therefore the $K_d$ between scFv-RG3 and rabbit IgG were $1.04 \times 10^{-8}$ M (PS/RG3), $9.45 \times 10^{-9}$ M (MUA/RG3). Table 2 lists the affinity constants of various engineered A10B scFvs binding with rabbit IgG antigen. Consistent with early results, the affinity constant for A10B RG3/MUA is highest. Affinity results for different sensor surfaces were list in Table 2.

Based on the Sauerbrey equation, a surface coverage of 238.3 ng/cm$^{-2}$, corresponding to $8.8 \times 10^{-11}$ mol/cm$^{-2}$ scFv-RG3, was obtained for the MUA modified QCM surface. The calculated surface coverage and binding efficiency for different scFv sensors are listed in Table 2.

TABLE 2

Surface coverage and binding efficiency.

| QCM sensors | Surface coverage (mol/cm$^2$) | Detection limit (nM) | Linear range (nM) | Ka (M$^{-1}$) |
|---|---|---|---|---|
| MUA/scFv-RG3 | $8.8 \times 10^{-11}$ | 0.2 | 0.2-33 | $10.6 \times 10^7$ |
| PSS/scFv-RG3 | $1.8 \times 10^{-10}$ | 0.33 | 0.33-33 | $9.6 \times 10^7$ |
| scFv-Cys | $1.74 \times 10^{-10}$ | 1.7 | 1.7-66 | $1.9 \times 10^7$ |
| scFv-His | $6.8 \times 10^{-11}$ | 2.3 | 2.3-33 | $5.2 \times 10^7$ |

Surface Rigidity: To test the rigidity of these sensor surfaces, QCM impedance analysis was used to determine the resonator impedance for the binding events as shown in FIG. 6 through FIG. 9. The change of damping resistances in all cases was smaller than 1.4% (Table 3).

TABLE 3

Changes in damping resistances ($|\Delta R_q|/R_q$) for experiments shown in FIG. 6 through FIG. 9.

| FIG. 6a A | 0.4% |
|---|---|
| FIG. 6a B | 0.7% |
| FIG. 6a C | 0.3% |
| FIG. 6a D | 0.3% |
| FIG. 6a E | 0.3% |
| FIG. 6a F | 0.8% |
| FIG. 6a G | 0.6% |
| FIG. 7 A | 0.2% |
| FIG. 7 B | 0.1% |
| FIG. 8 A | 0.4% |
| FIG. 8 B | 0.3% |
| FIG. 8 C | 0.5% |
| FIG. 8 D | 1.1% |
| FIG. 8 E | 1.1% |
| FIG. 8 F | 0.2% |
| FIG. 9 A | 0.7% |
| FIG. 9 B | 0.3% |
| FIG. 9 C | 0.6% |
| FIG. 10 A | 0.7% |
| FIG. 10 B | 0.4% |
| FIG. 10 C | 0.8% |
| FIG. 10 D | 0.03% |
| FIG. 10 E | 0.06% |
| FIG. 10 F | 0.6% |

Conclusions: Single chain antibodies (scFvs) obtained from phage display library allow rapid isolation of antibodies and their in vitro manipulation at the gene level. They represent smallest immuno-recognition elements, which provide an emerging strategy in the development of new immunosensors. Our early work demonstrated that scFv in which either a cysteine (C) amino acid or two histidines is incorporated into the (GGGGS)$_3$ peptide linker (GGGGS, SEQ ID NO:10) can self-assemble and be immobilized with correct orientation and high surface concentration on gold. When compared their performance with an IgG monoclonal antibody, the monoclonal IgG Fab and the scFv fragments of the IgG monoclonal antibody without cysteine or histidine in the linker for use in piezoimmunosensors to detect an antigen in a complex biological serum sample, the scFv-Cys or scFv-His immunosensor displayed greater assay sensitivity and exhibited less nonspecific adsorption. While our recent investigation have shown that by achieving a high degree of binding site orientation through scFv engineering, with relatively small size antibody fragments that allows much more dense packing of the binding site, the use of mass detection via QCM for direct antigen detection becomes a much more realistic analytical transduction approach for direct immunosensing. Challenges remain for the mass production and real world applications of scFv piezoimmunosensors. Even though literature show that in many scFvs there seems to be little effect of these linker variations on affinity or stability of the scFv. Certain amino acids in the linker sequence can affect the yield of functional Fvs that are obtained from refolding of inclusion bodies. For example, unpaired cysteines, particularly hydrophobic residues in the linker may reduce the yield of bacterial protein expression (J. Immun. Methods, 242 (2000)101-114). The successful implement scFv for immunosensing requires economically mass selection and production of scFvs using phage display techniques. In this report, we design the peptide linker sequence with cationic arginine charged residue periodicity to favor the adsorption at anionic charged template surface which facilitates the oriented immobilization of scFvs on the solid surface. Comparing to early scFv-cys, 10 fold further reduction of detection limits and one decade larger of dynamic range using A10B RG3 were observed. For amino acids, it is the side chain that gives each amino acid its identity. Protein engineering allows modifying individual protein molecules so that they are endowed with self-assembling capability in an oriented manner on the solid surface. As a result, With 20 amino acids to chose from, our strategy present a widely applicable technology for engineering scFv for immunosensing. The described general strategies could avoid the difficulty of protein expressions when active cysteine or histidine is incorporated and provide a general method to immobilize scFvs in an oriented, ordered or site directed manner on solid surface. We envision similar strategies that incorporate hydrophobic or hydrophilic residue periodicity to facilitate the adsorption on a non-polar or polar surface.

Example 2

This example is a surface plasmon resonance (SPR) study of 2-mercaptoethaol as a template in A10B scFv-YG immobilization.

Motivation: We have created an innovative immobilization method that is easy to operate, efficient, less costing and reliable in constructing biosensors for non-labeled immunoassay for understanding antibody and antigen interaction. Traditional immunoassays like ELISA are very reliable but is also a time- and cost-consuming process. For example, two antibodies that are specific for different sites on the same antigen are needed. It is not always easy to find such proper antibody pair for the assay. On the contrary, non-labeled immunosensors will do assays in a simple one step fashion. The sensing element, most likely the antibody, is immobilized on the surface of a transducer. When the antibody interacts with the antigen, mechanical or optical properties of the transducer are also changed. Such change is recorded and analyzed to provide information of the antibody-antigen interaction.

Background: The key component of antibody biosensors or immunosensors is the immobilized antibody present on the transducer surface. Immunosensors have been reported for detection and analysis of the pathogenic proteins, bacteria, and viruses. In order to improve the performance and sensitivity of immunosensors, our group has developed a technique which takes advantage of engineered recombinant single-chain fragment variable (scFv) antibody. Biosensors based on this technique are named scFv biosensors.

Figure 12:
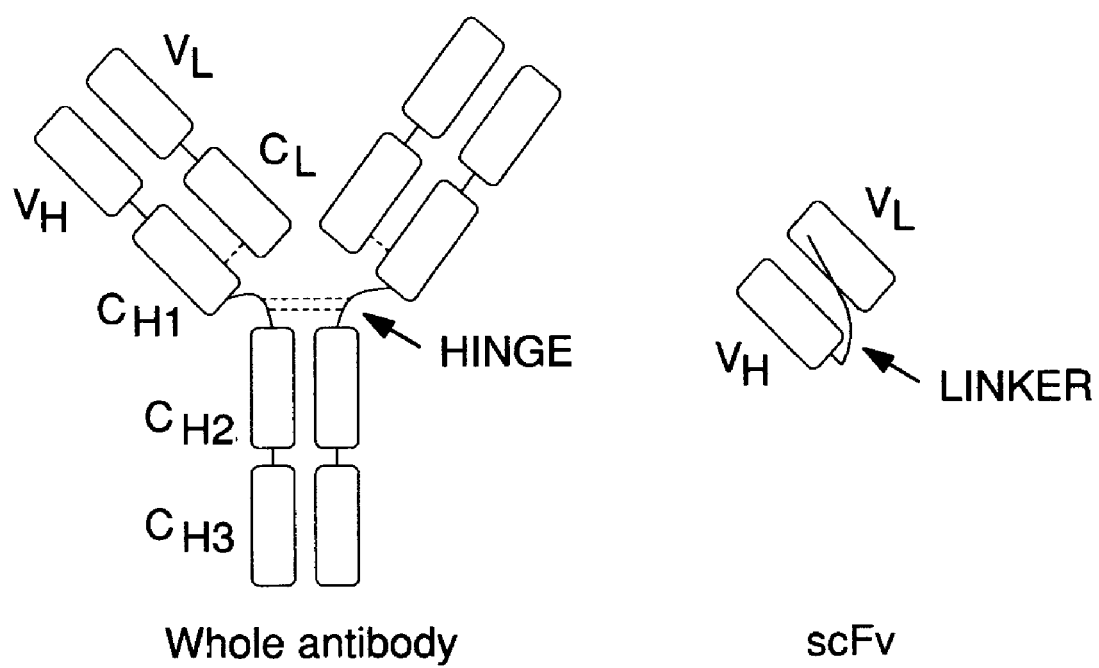
FIG. 12 is a representation of a whole antibody and a scFv, with the antibody heavy-chain ($V_H$) and light-chain ($V_L$) variable domains that are connected by a peptide linker to stabilize the molecule.

The scFv is the smallest portion of an antibody that retains the specificity and the function of recognition of antigen as illustrated in FIG. 12. It comprises the antibody heavy-chain ($V_H$) and light-chain ($V_L$) variable domains that are connected by a peptide linker to stabilize the molecule (FIG. 12). Compared to a whole antibody, the scFv is much smaller in size, making it possible to be immobilized on transducer surface with high density, which greatly increases the sensitivity. High density of sensing elements also allows us to perform a non-regeneration kinetic assay using non-labeled surface plasmon resonance (SPR) technique we developed.

Figure 13:
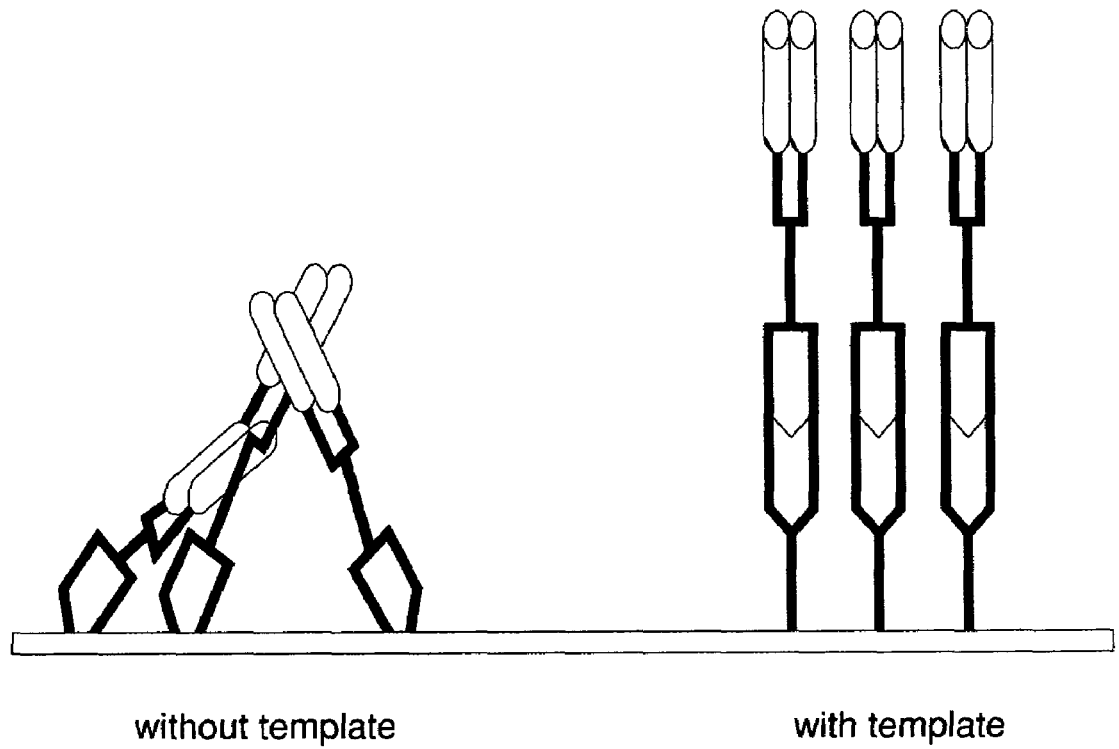
FIG. 13 shows the system without template (left) and with template (right), illustrating how the template helps the scFv to be immobilized with desired orientation.

One challenge in constructing scFv biosensors is the orientation of the immobilized scFv. Undesired orientation may deteriorate the performance of scFv biosensors. In this example, we develop immobilization methods that take advantage of the limitless flexibility of antibody engineering for the scFvs with the inherent quick, clean, high fidelity characters of surface coupling chemistry (e.g. electrostatic, hydrogen bonding or covalent attachment) to attach scFvs to a pre-formed functionalized self-assembled monolayer (SAM) template. Shown in FIG. 13, the template will help scFv to be immobilized with desired orientation, i.e. a monolayer of chemical molecules on the template will interact with the scFv linker so that the scFv is immobilized upright; therefore, the functional tip of scFv is pointing outwards in the solution phase without steric hindrance.

Innovation and Experiment: The selection of template is based on the sequence of the linker. The linker is a peptide containing 10-20 amino acids. In a YG linker, tyrosine is a potential hydrogen bond formation site because of the phenol group in tyrosine. Therefore, we propose to use 2-mercaptoethanol ($HS-CH_2-CH_2-OH$) as the template. The thiol group (HS—) of 2-mercaptoethanol helps the molecule to form a stable monolayer on transducer surface which is gold. The hydroxyl group (—OH) at the other end of 2-mercaptoethanol can form a hydrogen bond with the phenol group in the scFv linker. This bonding is strong enough to hold the scFv on the transducer surface as well as to keep the scFv in the desired orientation. To test this innovative idea, we will compare the performance of scFv immobilized through 2-mercaptoethanol to the performance of scFv immobilized directly on the transducer surface.

In this example, A10B anti-rabbit IgG scFv is used. Biosensors are constructed by means of direct immobilization or immobilization through 2-mercaptoethanol. The immobilization template is a piece of glass coated with gold, which is suited for SPR analysis.

Our innovative work on non-labeled antibody immunoassay shows many advantages over traditional immunoassay such as ELISA. In order for most traditional immunoassays to work, the assays need two antibodies that are specific for different sites on the same antigen. It can be extremely difficult and time-consuming to find pairs of antibodies that work in these assays even if there are a lot of antibodies to work with. The advantage of our non-labeled assay system is that only one antibody is needed to detect an antigen as well as the high sensitivity and specificity comparing to those immunosensors current available.

Experimental results: In the following experiment, a template, 2-mercaptoethanol, enhances the performance of A10B-YG scFv/A10B-FP1 scFv/A10B-ZnS4 scFv in recognizing rabbit IgG (r-IgG). As one amino acid in the YG/FP1/ZnS4 linker contains a phenol group and it can form hydrogen bonds with the hydroxyl group in 2-mercatoethanol, we expect the presence of the template can increase the amount and/or improve orientation of A10B-YG/FP1/ZnS4 scFv. Electrochemical impedance spectroscopy is used to verify the findings obtained by surface plasmon resonance (SPR).

Linker Peptide Sequences: The A10B scFv YG linker amino acid sequence is $YGGYG(GGGS)_2$, ie. YGGYGGGGSGGGS (SEQ ID NO:11) The A10B scFv FP1 linker amino acid sequence is SVSVGMKPSPRP (SEQ ID NO:4). The A10B scFvZnS4 linker amino acid sequence is VISNHAGSSRRL (SEQ ID NO:2).

Experimental.

All the SPR sensorgrams in the following part show the difference between two parallel sensors on two flow cells, i.e. FC1 and FC2. FC1 is used as reference cell, FC2 is used as sample cell.

The design of this experiment was to compare the template-immobilized scFv to the directly immobilized scFv side by side. Block reagent, such as BSA, was not used. The reference flow cell (FC1) was directly immobilized with A10B-YG scFv, while the sample flow cell (FC2) was immobilized with the same scFv through the template.

Figure 19:
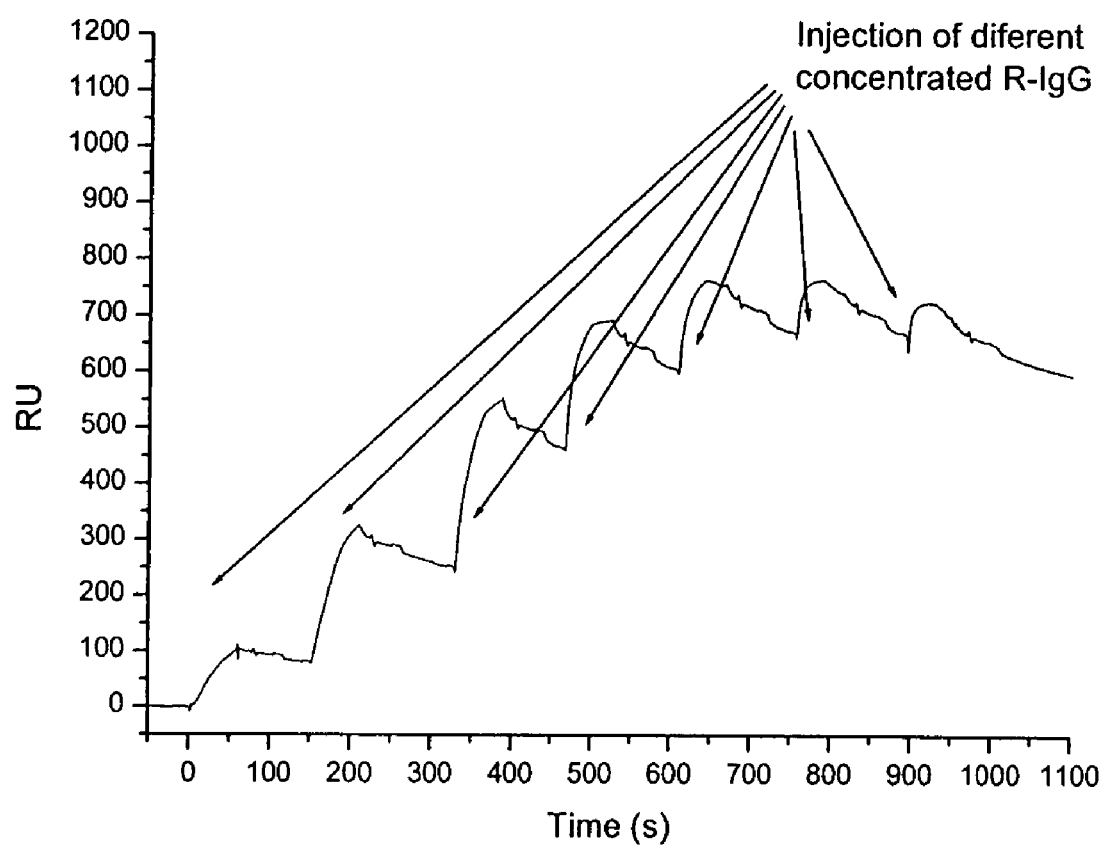
FIG. 19 shows the SPR response difference between A10B scFv-Cys biosensor reference cell (FC1) and sample cell (FC2). The graph contains seven injection steps that correspond to seven different concentrations of rabbit IgG, 6.25, 12.5, 25, 50, 100, and twice 200 µg/mL or 0.042, 0.083, 0.17, 0.33, 0.67, and twice 1.3 µM in that order. In this experiment, FC1 has the injection order of A10B-YG, R-IgG. FC2 has the injection order of 2-mercaptoethanol, A10B-YG, R-IgG.

FIG. 19 illustrates the SPR response difference between A10B scFv-Cys biosensor reference cell (FC1) and sample cell (FC2). The graph contains seven injection steps that correspond to seven different concentrations of rabbit IgG, 6.25, 12.5, 25, 50, 100, and twice 200 µg/mL or 0.042, 0.083, 0.17, 0.33, 0.67, and twice 1.3 µM in that order. In this experiment, FC1 has the injection order of A10B-YG, R-IgG. FC2 has the injection order of 2-mercaptoethanol, A10B-YG, R-IgG.

The same amount of R-IgG generated larger response on the flow cell with template indicating that the hydrogen bonding template allows better immobilization of scFvs. The response difference was about 700 RU.

Figure 20:
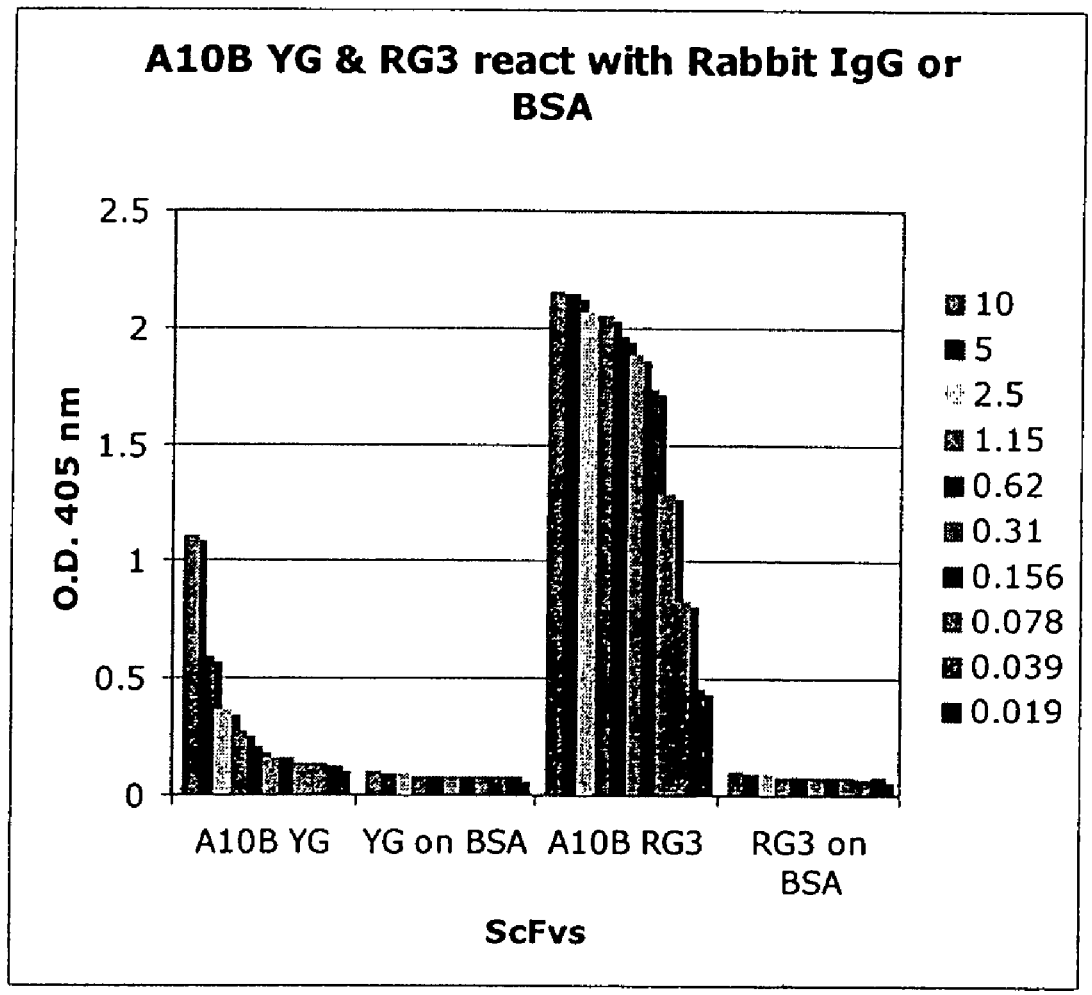
FIG. 20 shows ELISA results of sensitivity and specificity of A10B YG and A10B RG3.

FIG. 20 illustrates the ELISA results of sensitivity and specificity of A10B YG and A10B RG3. FIG. 20 shows the ELISA results of comparison of the sensitivity and specificity of A10B YG and RG3 when they react with rabbit IgG and BSA. Both A10B YG and RG3 has similar level of non-specific binding with BSA. But A10B YG has smaller sensitivity than A10B RG3. Amounts in descending order from left to right as listed in the key.

Figure 21:
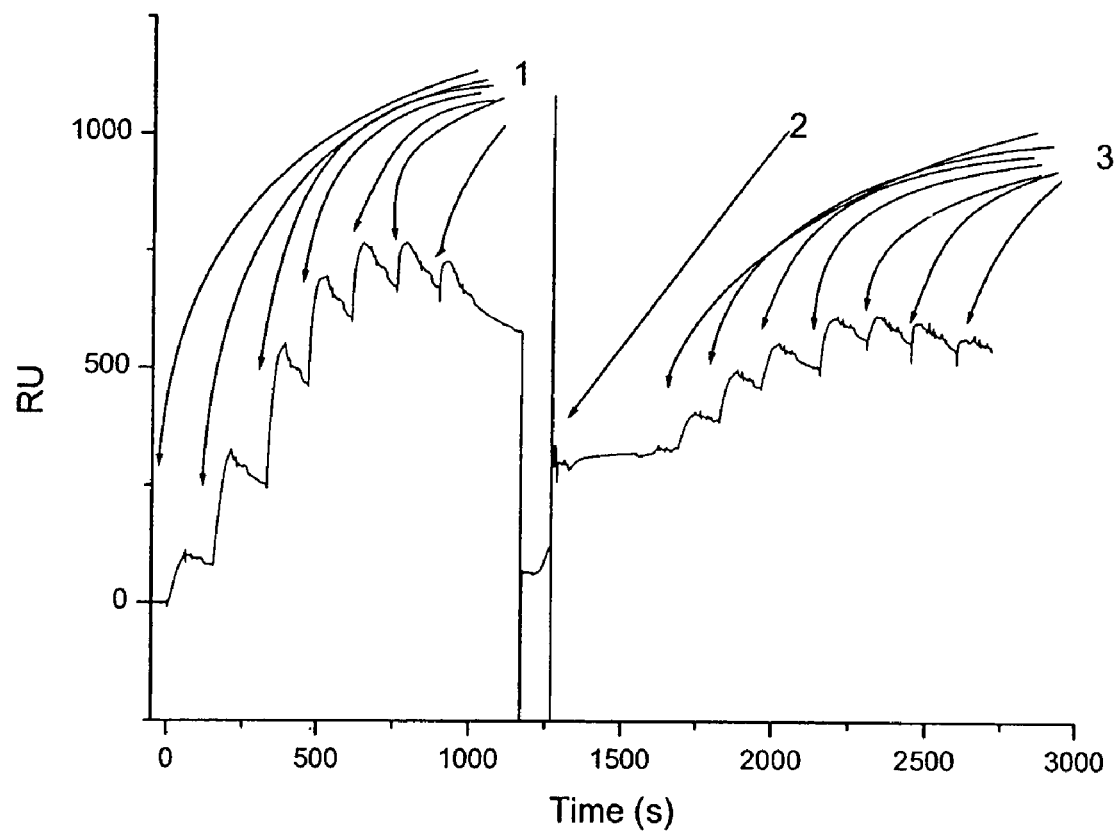
FIG. 21 shows in this experiment (1) FC1 has the injection order of A10B-YG, R-IgG. FC2 has the injection order of 2-mercaptoethanol, A10B-YG, R-IgG. (2) 30 µg/mL 0.3 M Zwittergent 3-08 pH 2.0. (3) repeat the experiment of (1)

Chip regeneration: FIG. 21 shows that 30 µg/mL 0.3 M Zwittergent 3-08 pH 2.0 was used to regenerate the sensor surface. Then it was reused to detect rabbit IgG. Some loss of the sensitivity was observed but the sensor could still gives reasonable response after the regeneration. When the regeneration process is optimized, we expect that the minimized sensitivity loss will be observed so that the sensor can have long life time. In this experiment, (1) FC1 has the injection order of A10B-YG, R-IgG. FC2 has the injection order of 2-mercaptoethanol, A10B-YG, R-IgG. (2)30 µg/mL 0.3 M Zwittergent 3-08 pH 2.0. (3) repeat the experiment of (1)

Discussion.

The direct immobilization of A10B-YG scFv on gold plate did not give acceptable result (Experiment 3) because the poorly orientated scFv limited the bioactivity of scFv.

In order to improve the performance of A10B-YG scFv, we proposed scFv immobilization through a template, 2-mercaptoethanol, utilizing the formation of hydrogen bonding between atoms O—H—O. The template improved the performance of A10B-YG scFv and retained its sensitivity and specificity.

Although the performance of A10B-YG can be improved with the help of a template, it still can not compare to the performance of A10B-cys. The A10B-YG sensor is saturated when the concentration of r-IgG reached 50 ug/mL while A10B-cys can go as high as 200 ug/mL. This could be due to the original low sensitivity of A10B YG comparing to A10B scFv-cys and A10B RG3, not due to the immobilization protocol.

Conclusion.

The idea has been verified that a poorly performed scFv can be improved by using template in immobilization. The most possible reason for 2-mercaptoethanol improving the immobilization of A10B-YG is due to the hydrogen bonding between atoms O—H—O or N—H—O.

Example 3

This example illustrates how scFv QCM can be used to detect bacteria. We have demonstrated that the scFv biosensor system can be used to provide a platform immobilization strategy to build rigid IgG Fc receptor layers. Just as important, the ability of immunoglobulins to react with other molecules at sites located outside the antigen-combining site, related to the effector functions of antibodies, are the most important part of the immune response including from such well-known reactions as the activation of the complement cascade and the activation or the inhibition of cells after binding with the Fc receptors to transportation of immunoglobulins through cell membranes. Shown in FIG. 1, monomeric scFv allows uniform 2:1 binding with rabbit IgG CH1 region, this results a highly oriented IgG Fc portion pointing toward solution phase for the detection of Fc receptors. This feasibility was proved by detection of Protein A, an Fc receptor on the cell wall of Staphylococcus aureus bacteria. Detection of protein A in bacteria is challenging due to the presence of excess antibody in the bacteria culture that often seriously suppresses the response of an assay by competing for the Fc binding sites on protein A thereby reducing the sensitivity of the assay. We demonstrated that the specific orientation of Fc capture agents consistently increases the analyte-binding capacity of the surfaces, with up to 7-fold improvements over surfaces with randomly oriented capture agents. Randomly attached IgG could not be packed at such a high density and had a lower specific activity. These results emphasize the importance of immobilization of capture reagents to surfaces such that their binding sites are oriented toward the solution phase.

The methods we demonstrated in this report can be quite general for building up rigid films for acoustic detection of various reagents from proteins to cell or bacterial. In contrast to SPR technique which probes the changes in the effective refractive index (RI) of the guided waves caused by the interactions of their evanescent field with analyte molecules binding specifically to their reaction partners immobilized on the sensor surfaces and has a limit of the thickness of the biofilms, i.e. less than 200 nm, QCM sensor detects only those materials that are acoustically coupled to the sensor surface and theoretically it has no limits about the thickness of the film. But it only requires the immobilized biofilms with high rigidity so it can acoustically couple with quartz oscillation. Since the peptide chain length, amino acid composition, specific sequence, net charge at neutral pH and hydrophobicity, all these features could be controlled and have dramatic influence on the performance of scFv based QCM sensors, For example, 15-mer unmodified peptides, there are ($\sim 10^{24}$) diverse sequences by considering the 20 common amino acids alone, Thus, the linker peptide design provides huge possibilities for surface coupling methodology. This feature, in conjunction with the real-time, non-labeled characters of QCM, presents a widely applicable protein immobilization technology for investigating the protein-protein interactions in general and promises QCM to be an indispensable technique in mapping the ligand-receptor interactions affordable to most investigators in life science research.

Chemicals and Materials.

Bacterial *Staphylococcus aureus* cultures and sample preparation: The bacterial *Staphylococcus aureus*, Cowan's serotype 1 that specific produce protein A was purchased from ATCC (Cat. number 12598, ATCC, Manassas, Va., USA). Bacteria was inoculated into 100 ml of Nutrient Broth culture medium contains 3.0 gm Beef Extract and 5.0 gm Peptone in one liter water, autoclave at 121° C. for 15 minutes. (Difco Cat. #233000, BD, Sparks, Md., USA). Bacteria were incubated at 37° C. for overnight with shaking at 150 rpm. The bacterial was then centrifuge down at 4,000 rpm. Supernatant was discarded. The bacteria were washed three times by re-suspended pellet in PBS and centrifuge at same speed as above. The washed *Staphylococcus aureus* bacteria were collected into microcentrifuge tubes for assay. To remove bacteria surface bound IgG, bacteria sample was well re-suspended in 0.1 M Na-citric acid elution buffer (pH 2.8) for 10 minutes, washed three times by PBS to neutralize pH to 7.0 and centrifuge at 4,000 rpm. The cell numbers were counted by using a hemacytometer counting chamber.

A10B ScFv immobilization: The non-polished gold quartz surface was cleaned sequentially with mixed concentrated acid solution ($H_2SO_4/HNO_3$ in 1:1 v/v), biograde water, and ethanol three times. Then, the surface was rinsed with biograde water and dried with nitrogen. The freshly washed gold surface was first immersed either into 4 mM MUA solution overnight or in 2 mg/ml PSS solution for 1-2 hours to form self-assembly anionic charged layer. The anionic charged gold surface was then immersed into A10B scFv-RG3 solution for 8 hours, followed by the treatment of blocking reagent, 0.1% BSA, for 0.5 hour. After the incubation, the excess scFvs on the surface of QCM was washed away with PBS buffer and biograde water. The MUA/scFv-RG3 or PSS/scFv-RG3 modified surface was dried under nitrogen, and used for the detection. A similar procedure was applied to form the PSS/scFv-RG3 modified surface.

QCM measurements: The gold quartz crystal electrode used through out this study was AT cut quartz that coated with 1000 Å gold in ~0.23 cm² geometric area (International Crystal Company, Oklahoma). It was cleaned as above and modified with scFvs. Then it was mounted in a Kel-F cell sealed by two O-rings and filled with 1 mL PBS buffer. The cell was continuously stirred during the measurement and was placed in a Faraday cage to reduce the potential electromagnetical noise. The frequency change and the damping resistance change caused by the analyte addition were monitored by the Network/Spectrum/Impedance Analyzer (Agilent 4395A).

Results and Discussion.

QCM analysis of purified protein A: The orientated immobilization of scFv-RG3 on the MUA surface specifically bound with the CH1 domain of the rabbit IgG to form what is referred to as an MUA/scFv-RG3/IgG surface. This made the IgG Fc portion available in a highly packed manner. The highly oriented IgG Fc layer could be applied for the detection of Fc receptors. Protein A, a well-known Fc receptor, is able to specifically bind to the Fc portion of various classes and subclasses of immunoglobins, and especially to IgG. Thus, we selected purified protein A as a model sample to examine the detection ability of an Fc receptor via our immobilization strategy.

Figure 14:
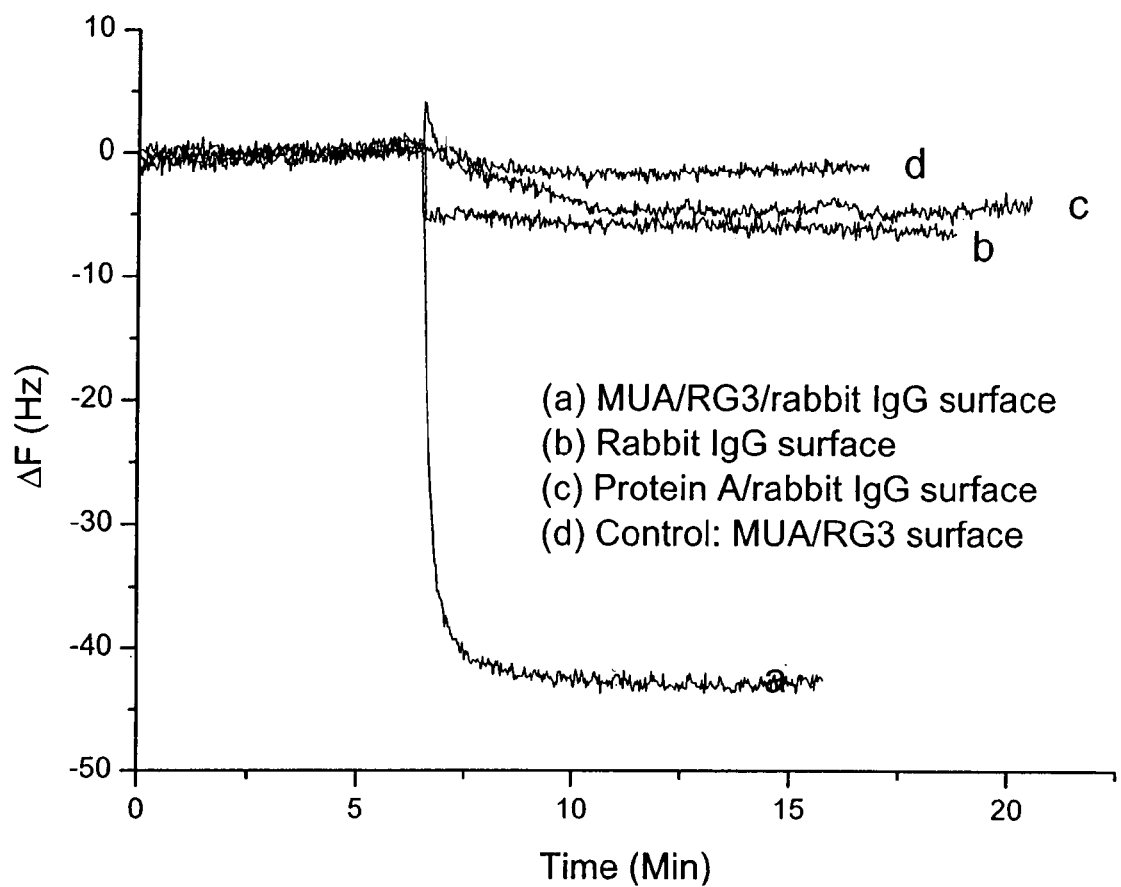
FIG. 14 shows frequency change vs. time curves when protein A was added to (a) MUA/scFv-RG3 coupling with rabbit IgG surface (MUA/scFv-RG3/IgG surface); (b) randomly orientated rabbit IgG surface; (c) rabbit IgG coupling onto the protein A surface; (d) MUA/scFv-RG3 surface without rabbit IgG (negative control).

Addition of purified protein A sample to the MUA/scFv-RG3/IgG surface (ie. the rabbit IgG was already bound to the MUA/scFv-RG3 modified surface) produced a 47 Hz signal response. This signal is about 7-fold increase over randomly orientated rabbit IgG surface and protein A/IgG surface (rabbit IgG was coupled onto the protein A surface) (FIG. 14). To investigate the specificity of the protein A detection, the MUA/scFv-RG3 sensor surface in the absence of rabbit IgG was used as negative control. The addition of protein A to the control surface only generated a very small frequency decrease (FIG. 14 Curve d). FIG. 14 illustrates frequency change vs. time curves when protein A was added to (a) MUA/scFv-RG3 coupling with rabbit IgG surface (MUA/scFv-RG3/IgG surface); (b) randomly orientated rabbit IgG surface; (c) rabbit IgG coupling onto the protein A surface; (d) MUA/scFv-RG3 surface without rabbit IgG (negative control).

Figure 15:
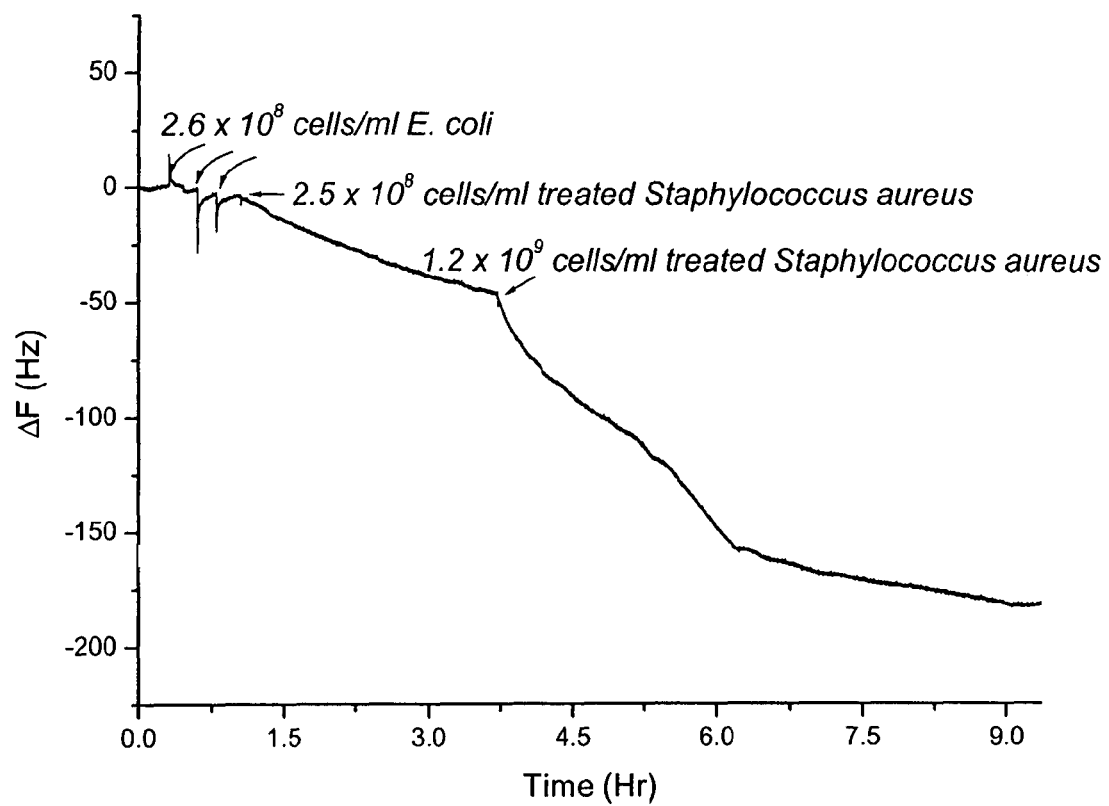
FIG. 15 shows frequency vs. time curves. MUA/scFv-RG3/IgG surface was exposed to $2.6 \times 10^{-8}$ cells/ml E. coli (negative control,), followed by the addition of Staphylococcus aureus ($2.5 \times 10^{-8}$ cells/ml, $1.2 \times 10^{-9}$ cells/ml).

QCM analysis of Staphylococcus aureus: In order to examine the sensor selectivity, E. coli was utilized as a negative control. The addition of E. coli to MUA/scFv-RG3/IgG sensor gave a really small signal response. After the exposure to E. coli, Staphylococcus aureus, gram-positive bacteria that possess protein A on cell surface, were consecutively added to the sensor. (The Staphylococcus aureus sample was pre-treated by 0.1 M Na-citric acid elution buffer (pH 2.8) to remove the IgG bond on the surface). FIG. 15 shows frequency vs. time curves. MUA/scFv-RG3/IgG surface was exposed to $2.6 \times 10^8$ cells/ml E. coli (negative control,), followed by the addition of Staphylococcus aureus ($2.5 \times 10^8$ cells/ml, $1.2 \times 10^9$ cells/ml). Large response signals were observed upon the addition of Staphylococcus aureus sample (FIG. 15). This result indicated that the sensor has good selectivity toward Staphylococcus aureus, and the sensor can remain the high sensitivity toward Staphylococcus aureus even in a complex solution system.

Figure 16:
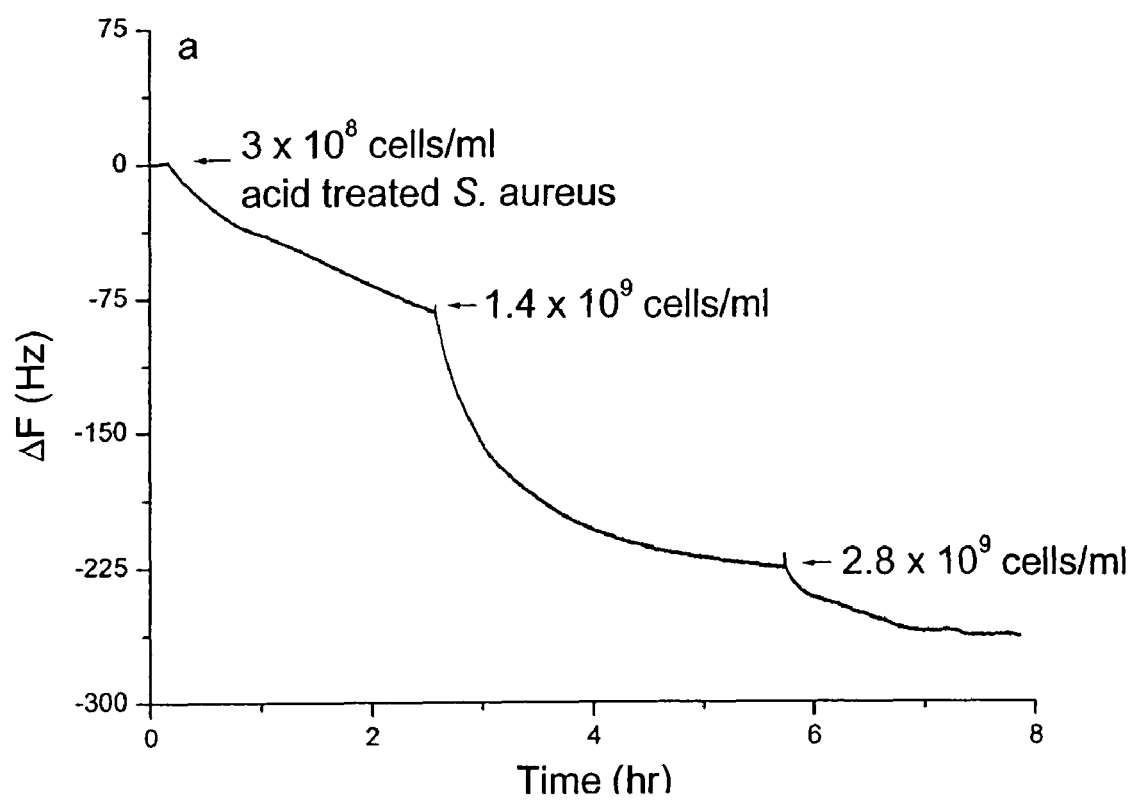
FIG. 16 shows the frequency vs, time curve when different concentrations of Staphylococcus aureus were added to MUA/scFv-RG3 coupling with rabbit IgG surface.

Binding Study: FIG. 16 shows the frequency vs, time curve when different concentrations of Staphylococcus aureus samples were added to MUA/scFv-RG3 coupling with rabbit IgG surface.

Figure 17:
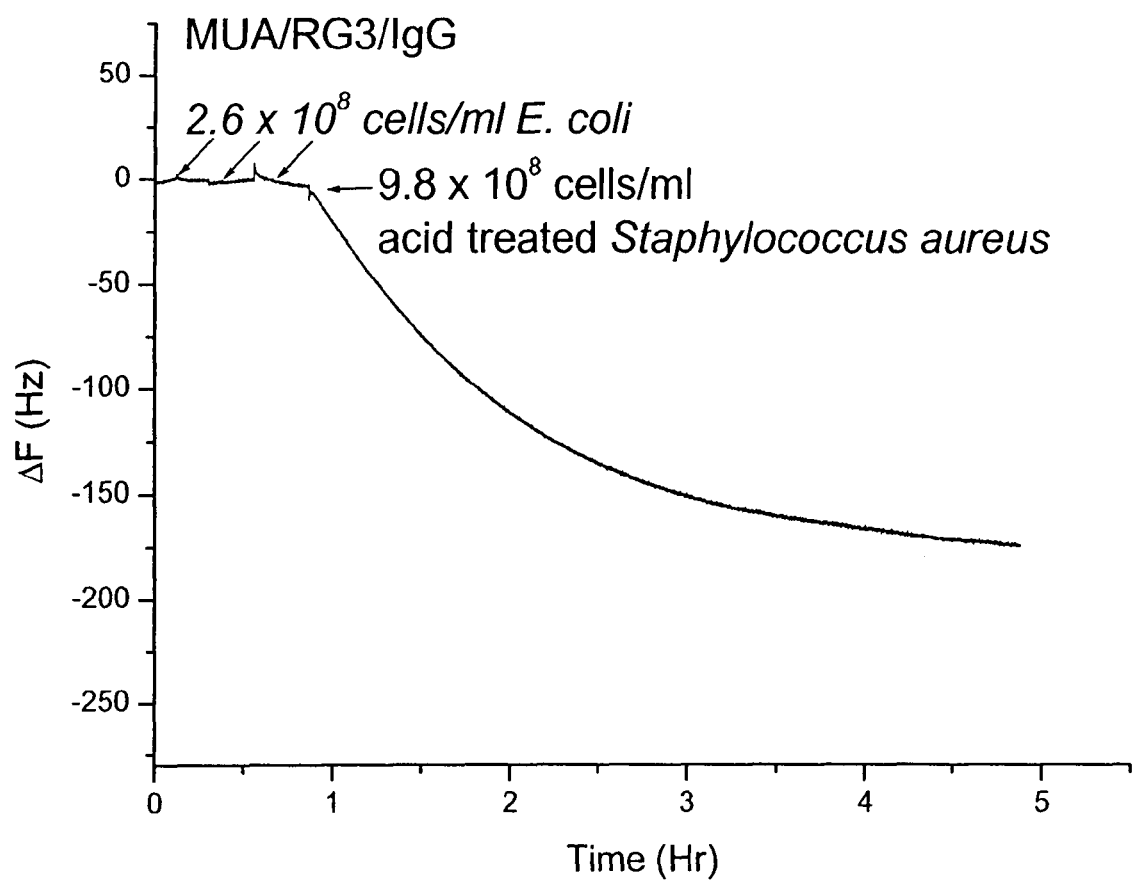
FIG. 17 shows the frequency vs, time curve when MUA/scFv-RG3 coupling with rabbit IgG surface was exposed to $2.6 \times 10^{-8}$ cells/ml E. coli (negative control) and Staphylococcus aureus.

Selectivity Test: FIG. 17 shows the frequency vs, time curve when MUA/scFv-RG3 coupling with rabbit IgG surface was exposed to $1.5 \times 10^8$ cells/ml E. coli (negative control) and $9.8 \times 10^8$ cells/ml Staphylococcus aurenus.

Figure 18:
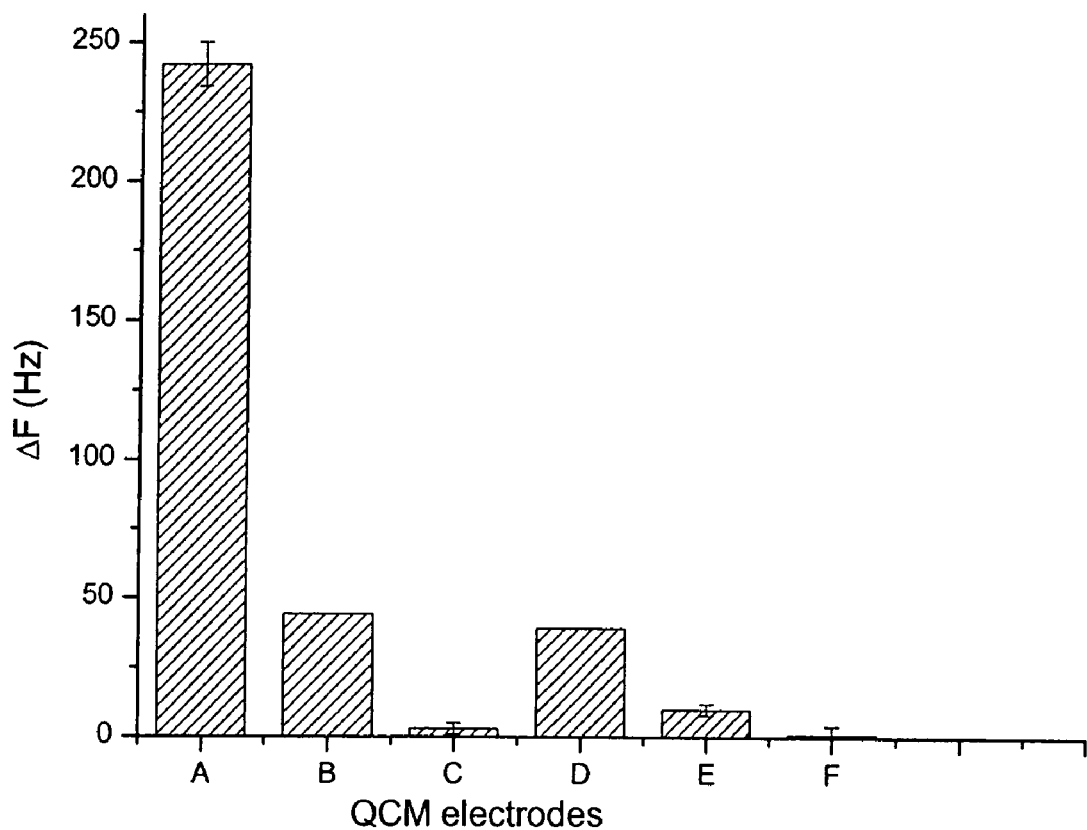
FIG. 18 shows the comparison of sensor specificity. $1.4 \times 10^9$ cells/ml acid treated Staphylococcus aureus was added to rabbit IgG treated MUA/scFv-RG3 sensor (Bar A); $1.4 \times 10^9$ cells/ml non-treated Staphylococcus aureus was added to rabbit IgG treated MUA/scFv-RG3 sensor (Bar B); $2.6 \times 10^8$ cells/ml E. coli was added to rabbit IgG treated MUA/scFv-RG3 sensor (Bar C). (D-F control surfaces) $1.4 \times 10^9$ cells/ml acid treated Staphylococcus aureus were added to random orientated rabbit IgG surface (D); MUA/scFv-RG3 surface (without rabbit IgG) surface (E); and mannose surface (F).

In order to test the sensor specificity, several control experiments were then performed. (FIG. 18). Different samples were added to the MUA/scFv-RG3/IgG sensors. The addition of Staphylococcus aureus sample ($1.4 \times 10^9$ cell/ml) that was pre-treated with acid to remove all surface IgG to generate a large frequency change (~230-250 Hz, Bar A). Staphylococcus aureus without acid treatment ($1.4 \times 10^9$ cell/ml) gave only ~44 Hz frequency change (Bar B). This ~6 times signal reduction suggested that some protein A on the Staphylococcus aureus surface have been occupied already by the surface bond IgG. Thus, removal of the IgG from the bacterial surface can dramatically increase the sensitivity of the sensor. E. coli, a gram-negative bacterium, was applied as negative control reagent, and generated really small frequency change (5 Hz, Bar C).

The directly immobilized rabbit IgG surface (Bar D), MUA/scFv-RG3 surface (without the treatment of rabbit IgG) (Bar E), and mannose modified QCM surfaces (specifically bind to ConA) (Bar F) were selected as control surfaces. The addition of the same concentration of acid treated Staphylococcus aureus generated ~39 Hz frequency change to the random orientated rabbit IgG surface (Bar D), ~10 Hz non-specific absorption to the MUA/scFv-RG3 surface (without rabbit IgG) (Bar E) and no detectable nonspecific absorption to the mannose modified QCM surfaces (Bar F).

All these control experiments confirmed that the MUA/scFv-RG3/IgG surface is highly selective for the detection Staphylococcus aureus via the specific binding between Fc portion of rabbit IgG and cell surface protein A.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

We claim:

1. A method of detecting an analyte of interest in a sample, the method comprising:
    (a) providing the sample;
    (b) providing an immunosensor device having a component apparatus for binding the analyte of interest in a sample, the apparatus comprising:
        (i) a solid substrate with an exposed surface;
        (ii) a compound provided as a layer bound on the solid substrate; and
        (iii) a plurality of recombinant single chain antibodies (scFv's) specific for the analyte of interest bound to the compound on the solid substrate, each scFv comprising:
            (A) an antibody variable light chain ($V_L$) polypeptide specific for an analyte,
            (B) an antibody variable heavy chain ($V_H$) polypeptide specific for the analyte, and
            (C) a linker polypeptide covalently linking the antibody variable light chain ($V_L$) polypeptide to the antibody variable heavy chain ($V_H$) polypeptide, the linker polypeptide having an amino acid sequence comprising one or more amino acids with sidechains that bind to the compound,
        wherein when the analyte of interest is present in the sample the scFv binds the analyte to the solid substrate;
    (c) applying the sample to the apparatus for a time sufficient for the scFv on the substrate to bind to the analyte if present in the sample; and
    (d) detecting the analyte bound to the scFv on the solid substrate with the immunosensor device.

2. The method of claim 1, wherein the immunosensor device is a quartz crystal microbalance (QCM) device, a surface plasmon resonance (SPR) device, or an electrochemical impedance analyzer device.

3. The method of claim 1, wherein the compound and the amino acid sidechains form electrostatic interactions.

4. The method of claim 1, wherein the compound and the amino acid sidechains form hydrogen bonds.

5. The method of claim 1, wherein the compound and the amino acid sidechains form hydrophobic interactions.

6. The method of claim 1, wherein the amino acids with sidechains are arginine or tyrosine.

7. The method of claim 1, wherein the compound is electrostatically charged.

8. The method of claim 1, wherein the compound comprises negatively charged amino acids.

9. The method of claim 1, wherein the compound is an anionic polyelectrolyte or 2-mercaptoethanol.

10. The method of claim 1, wherein the compound is an anionic polyelectrolyte selected from the group consisting of poly(sodium 4-styrenesulfonate) (PSS) and 11-mercaptoundecanoic acid (MUA).

11. The method of claim 1, wherein the substrate is gold.

12. The method of claim 1, wherein the amino acids with sidechains are separated by one or more spacer amino acids.

13. The method of claim 1, wherein the spacer amino acids are selected from the group consisting of glycine and serine.

14. The method of claim 1, wherein the amino acid sequence of the linker polypeptide comprises a series of two or more arginine-glycine (RG) repeats.

15. The method of claim 1, wherein the amino acid sequence of the linker polypeptide comprises a sequence selected from the group consisting of SEQ ID NO:1, SEQ ID NO:2, SEQ ID NO:3, SEQ ID NO:4, SEQ ID NO:5, SEQ ID NO:11, and SEQ ID NO:12.

16. A method of binding an analyte of interest in a sample, the method comprising:
    (a) providing the sample;
    (b) providing an apparatus for binding an analyte of interest in a sample, the apparatus comprising:
        (i) a solid substrate with an exposed surface;
        (ii) a compound provided as a layer bound on the solid substrate; and
        (iii) a plurality of recombinant single chain antibodies (scFv's) specific for the analyte of interest bound to the compound on the solid substrate, each scFv comprising:
            (A) an antibody variable light chain ($V_L$) polypeptide specific for an analyte,
            (B) an antibody variable heavy chain ($V_H$) polypeptide specific for the analyte, and
            (C) a linker polypeptide covalently linking the antibody variable light chain ($V_L$) polypeptide to the antibody variable heavy chain ($V_H$) polypeptide, the linker polypeptide having an amino acid sequence comprising one or more amino acids with sidechains that bind to the compound,
        wherein when the analyte of interest is present in the sample the scFv binds the analyte to the solid substrate; and
    (c) incubating the sample to the apparatus for a time sufficient for the scFv on the solid substrate to bind to the analyte if present in the sample.

17. The method of claim 16, wherein the apparatus is a microtiter plate for an ELISA assay or a microarray.

18. The method of claim 16, wherein the apparatus is an affinity column.

19. The method of claim 16, wherein the compound and the amino acid sidechains form electrostatic interactions.

20. The method of claim 16, wherein the compound and the amino acid sidechains form hydrogen bonds.

21. The method of claim 16, wherein the compound and the amino acid sidechains form hydrophobic interactions.

22. The method of claim 16, wherein the amino acids with sidechains are arginine or tyrosine.

23. The method of claim 16, wherein the compound is electrostatically charged.

24. The method of claim 16, wherein the compound comprises negatively charged amino acids.

25. The method of claim 16, wherein the compound is an anionic polyelectrolyte or 2-mercaptoethanol.

26. The method of claim 16, wherein the compound is an anionic polyelectrolyte selected from the group consisting of poly(sodium 4-styrenesulfonate) (PSS) and 11-mercaptoundecanoic acid (MUA).

27. The method of claim 16, wherein the substrate is gold.

28. The method of claim 16, wherein the amino acids with sidechains are separated by one or more spacer amino acids.

29. The method of claim 16, wherein the spacer amino acids are selected from the group consisting of glycine and serine.

30. The method of claim 16, wherein the amino acid sequence of the linker polypeptide comprises a series of two or more arginine-glycine (RG) repeats.

31. The method of claim 16, wherein the amino acid sequence of the linker polypeptide comprises a sequence selected from the group consisting of SEQ ID NO:1, SEQ ID NO:2, SEQ ID NO:3, SEQ ID NO:4, SEQ ID NO:5, SEQ ID NO:11, and SEQ ID NO:12.

* * * * *

SEQUENCE LISTING

```
<160> NUMBER OF SEQ ID NOS: 15

<210> SEQ ID NO 1
<211> LENGTH: 11
<212> TYPE: PRT
<213> ORGANISM: Artificial
<220> FEATURE:
<223> OTHER INFORMATION: linker peptide RG3

<400> SEQUENCE: 1

Arg Gly Arg Gly Arg Gly Arg Gly Arg Gly Arg
1               5                   10

<210> SEQ ID NO 2
<211> LENGTH: 12
<212> TYPE: PRT
<213> ORGANISM: Artificial
<220> FEATURE:
<223> OTHER INFORMATION: linker peptide ZnS4

<400> SEQUENCE: 2

Val Ile Ser Asn His Ala Gly Ser Ser Arg Arg Leu
1               5                   10
```

```
<210> SEQ ID NO 3
<211> LENGTH: 12
<212> TYPE: PRT
<213> ORGANISM: Artificial
<220> FEATURE:
<223> OTHER INFORMATION: linker peptide CdS6

<400> SEQUENCE: 3

Pro Trp Ile Pro Thr Pro Arg Pro Thr Phe Thr Gly
1               5                   10

<210> SEQ ID NO 4
<211> LENGTH: 12
<212> TYPE: PRT
<213> ORGANISM: Artificial
<220> FEATURE:
<223> OTHER INFORMATION: linker peptide FP1

<400> SEQUENCE: 4

Ser Val Ser Val Gly Met Lys Pro Ser Pro Arg Pro
1               5                   10

<210> SEQ ID NO 5
<211> LENGTH: 15
<212> TYPE: PRT
<213> ORGANISM: Artificial
<220> FEATURE:
<223> OTHER INFORMATION: linker peptide RG3 15-mer

<400> SEQUENCE: 5

Arg Gly Arg Gly Arg Gly Arg Gly Arg Ser Arg Gly Gly Gly Ser
1               5                   10                  15

<210> SEQ ID NO 6
<211> LENGTH: 4
<212> TYPE: PRT
<213> ORGANISM: Artificial
<220> FEATURE:
<223> OTHER INFORMATION: RG peptide

<400> SEQUENCE: 6

Arg Gly Arg Gly
1

<210> SEQ ID NO 7
<211> LENGTH: 13
<212> TYPE: PRT
<213> ORGANISM: Artificial
<220> FEATURE:
<223> OTHER INFORMATION: E-tag peptide

<400> SEQUENCE: 7

Gly Ala Pro Val Pro Tyr Pro Asp Pro Leu Glu Pro Arg
1               5                   10

<210> SEQ ID NO 8
<211> LENGTH: 15
<212> TYPE: PRT
<213> ORGANISM: Artificial
<220> FEATURE:
<223> OTHER INFORMATION: linker peptide Cys

<400> SEQUENCE: 8

Cys Gly Gly Gly Ser Gly Gly Gly Ser Gly Gly Gly Gly Ser
1               5                   10                  15
```

```
<210> SEQ ID NO 9
<211> LENGTH: 15
<212> TYPE: PRT
<213> ORGANISM: Artificial
<220> FEATURE:
<223> OTHER INFORMATION: linker peptide RS

<400> SEQUENCE: 9

Gly Gly Gly Gly Ser Gly Gly Gly Ser Gly Gly Gly Gly Ser
1               5                   10                  15

<210> SEQ ID NO 10
<211> LENGTH: 5
<212> TYPE: PRT
<213> ORGANISM: Artificial
<220> FEATURE:
<223> OTHER INFORMATION: GGGGS peptide fragment

<400> SEQUENCE: 10

Gly Gly Gly Gly Ser
1               5

<210> SEQ ID NO 11
<211> LENGTH: 13
<212> TYPE: PRT
<213> ORGANISM: Artificial
<220> FEATURE:
<223> OTHER INFORMATION: linker peptide YG

<400> SEQUENCE: 11

Tyr Gly Gly Tyr Gly Gly Gly Gly Ser Gly Gly Gly Ser
1               5                   10

<210> SEQ ID NO 12
<211> LENGTH: 15
<212> TYPE: PRT
<213> ORGANISM: Artificial
<220> FEATURE:
<223> OTHER INFORMATION: linker peptide WG

<400> SEQUENCE: 12

Trp Gly Gly Tyr Ser Gly Gly Gly Gly Ser Gly Gly Gly Gly Ser
1               5                   10                  15

<210> SEQ ID NO 13
<211> LENGTH: 15
<212> TYPE: PRT
<213> ORGANISM: Artificial
<220> FEATURE:
<223> OTHER INFORMATION: linker peptide C4 and C-11

<400> SEQUENCE: 13

Ser His Gly Gly His Gly Gly Gly Gly Ser Gly Gly Gly Gly Ser
1               5                   10                  15

<210> SEQ ID NO 14
<211> LENGTH: 5
<212> TYPE: PRT
<213> ORGANISM: Artificial
<220> FEATURE:
<223> OTHER INFORMATION: His-tag of A10B scFv C-11

<400> SEQUENCE: 14

His His His His His
1               5

<210> SEQ ID NO 15
```

-continued

```
<211> LENGTH: 15
<212> TYPE: PRT
<213> ORGANISM: Artificial
<220> FEATURE:
<223> OTHER INFORMATION: linker peptide MG4

<400> SEQUENCE: 15

Met Gly Gly Met Ser Gly Gly Gly Ser Gly Gly Gly Gly Ser
1               5                   10                  15
```